United States Patent
Khanicheh et al.

(10) Patent No.: US 10,881,838 B2
(45) Date of Patent: Jan. 5, 2021

(54) ENDOSCOPIC BALLOON CATHETER

(71) Applicant: HOYA Corporation, Tokyo (JP)

(72) Inventors: Azadeh Khanicheh, Somerville, MA (US); Isaac Ostrovsky, Wellesley, MA (US); Almir Velagic, Watertown, MA (US); Michael Barenboym, Boston, MA (US)

(73) Assignee: HOYA CORPORATION, Tokyo (JP)

( * ) Notice: Subject to any disclaimer, the term of this patent is extended or adjusted under 35 U.S.C. 154(b) by 528 days.

(21) Appl. No.: 15/653,717

(22) Filed: Jul. 19, 2017

(65) Prior Publication Data
US 2019/0022359 A1    Jan. 24, 2019

(51) Int. Cl.
*A61M 25/10* (2013.01)
*A61B 1/00* (2006.01)
(Continued)

(52) U.S. Cl.
CPC ......... *A61M 25/10* (2013.01); *A61B 1/00137* (2013.01); *A61M 25/0032* (2013.01);
(Continued)

(58) Field of Classification Search
CPC .... A61M 25/09041; A61M 2025/1056; A61M 25/0138; A61M 2025/0024; A61M 2025/018; A61M 25/0015; A61M 25/0169; A61M 25/0097; A61M 2025/0177; A61M 2025/0188; A61M 2025/0681; A61B 1/00085; A61B 1/0014; A61B 1/00121
See application file for complete search history.

(56) References Cited

U.S. PATENT DOCUMENTS

| 4,988,356 A | * | 1/1991 | Crittenden | ........ | A61M 25/0169 |
| | | | | | 600/434 |
| 6,849,077 B2 | * | 2/2005 | Ricci | ................... | A61M 25/104 |
| | | | | | 606/108 |

(Continued)

OTHER PUBLICATIONS

Notification of Transmittal of the International Search Report and Written Opinion of the International Searching Authority in corresponding PCT International Application No. PCT/IB2018/055360 (21 pages).

(Continued)

*Primary Examiner* — Nathan R Price
*Assistant Examiner* — Melissa A Snyder
(74) *Attorney, Agent, or Firm* — Finnegan, Henderson, Farabow, Garrett & Dunner, L.L.P.

(57) ABSTRACT

Embodiments of the present disclosure are directed to apparatuses, systems, and methods for merging a balloon catheter onto a locked guidewire. In one implementation, a balloon catheter may include an inflatable balloon affixed thereto and a slit extending from a distal end of a guidewire lumen to a position proximal of the balloon. The slit may be widened by a working member of an adapter to allow passage of the locked guidewire into the guidewire lumen of the balloon catheter. The balloon catheter may be merged onto the guidewire via the slit and delivered to the desired treatment device without requiring the guidewire to be unlocked. Advantageously, access to at least one desired treatment site may be maintained with the guidewire during merging of the balloon catheter.

30 Claims, 25 Drawing Sheets

(51) Int. Cl.
A61M 25/01 (2006.01)
A61M 25/00 (2006.01)
*A61B 1/018* (2006.01)

(52) U.S. Cl.
CPC .... *A61M 25/0097* (2013.01); *A61M 25/0169* (2013.01); *A61M 25/1002* (2013.01); *A61B 1/00133* (2013.01); *A61B 1/018* (2013.01); *A61M 25/0015* (2013.01); *A61M 25/1011* (2013.01); *A61M 2025/0183* (2013.01); *A61M 2025/0188* (2013.01); *A61M 2025/1004* (2013.01); *A61M 2025/107* (2013.01); *A61M 2025/1075* (2013.01)

(56) References Cited

U.S. PATENT DOCUMENTS

| | | | |
|---|---|---|---|
| 6,893,393 B2* | 5/2005 | Carrillo | A61M 25/02 600/104 |
| 7,172,577 B2 | 2/2007 | Mangano et al. | |
| 7,645,283 B2 | 1/2010 | Reynolds et al. | |
| 2003/0233043 A1 | 12/2003 | Windheuser et al. | |
| 2004/0143286 A1* | 7/2004 | Johnson | A61F 2/856 606/194 |
| 2005/0059990 A1 | 3/2005 | Ayala et al. | |
| 2012/0197378 A1 | 8/2012 | Houser | |
| 2015/0011834 A1 | 1/2015 | Ayala et al. | |

OTHER PUBLICATIONS

Boston Scientific Corporation, May 2016, "Dreamtome RX Sphincterotome" Brochure ENDO-377607-AA (6 pages).
Boston Scientific Corporation, May 2016, "Trapezoid™ RX" ENDO-333814-AA (4 pages).
Boston Scientific Corporation, Jun. 2016, "Extractor™ Pro RX-S" ENDO-396406-AA (2 pages).
U.S. Appl. No. 15/585,487; System and Methods for Device Exchange in an Endoscopic Procedure; Azadeh Khanicheh et al; filed May 3, 2017.
U.S. Appl. No. 15/653,737; Universal Retrieval Device for Removing Obstructions From Body Lumens; Isaac Ostrovsky et al; filed Jul. 19, 2017.
U.S. Appl. No. 15/653,727; Endoscopic Basket Delivery Catherter; Azadeh Khanicheh et al; filed Jul. 19, 2017.
U.S. Appl. No. 15/653,731; Endoscopic Cannulating Devices and Methods of USE; Azadeh Khanicheh et al; filed Jul. 19, 2017.

* cited by examiner

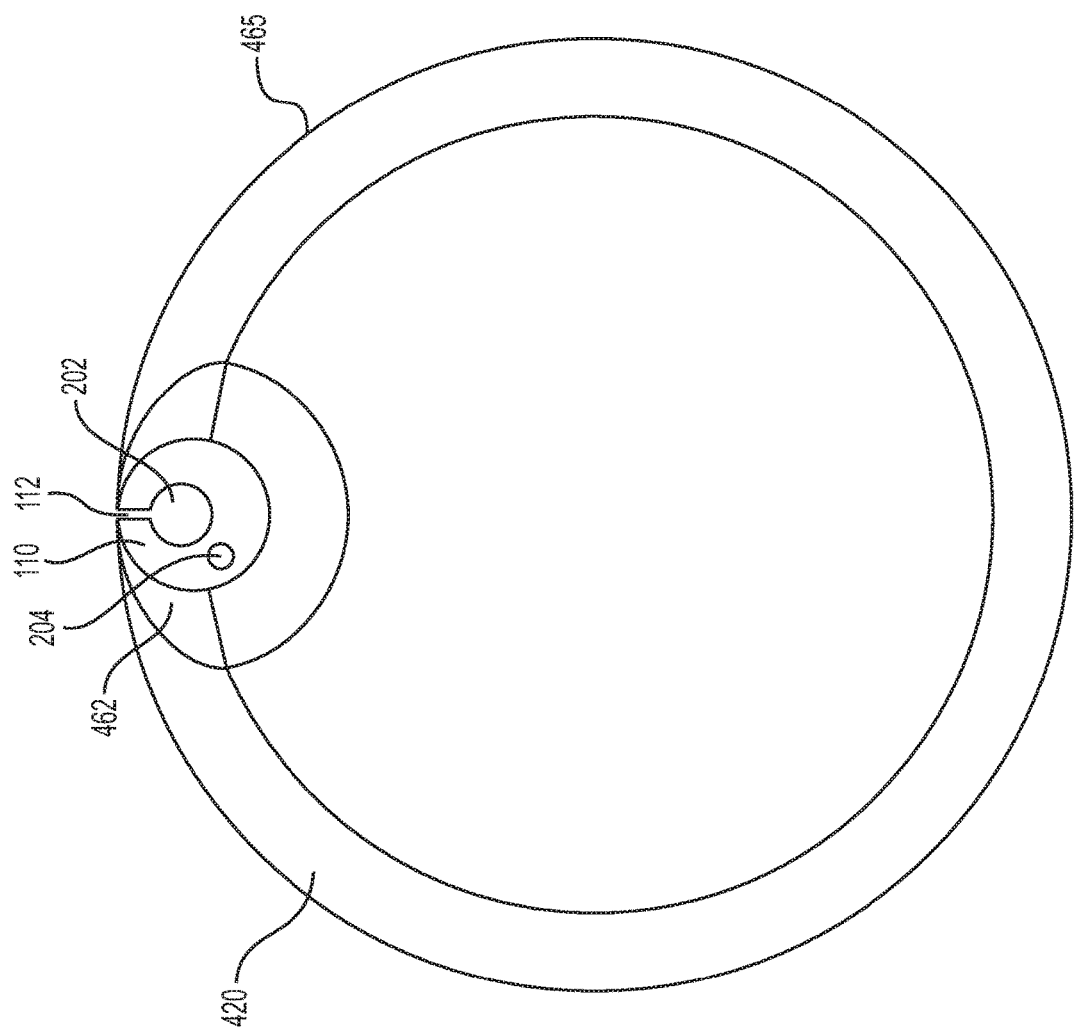

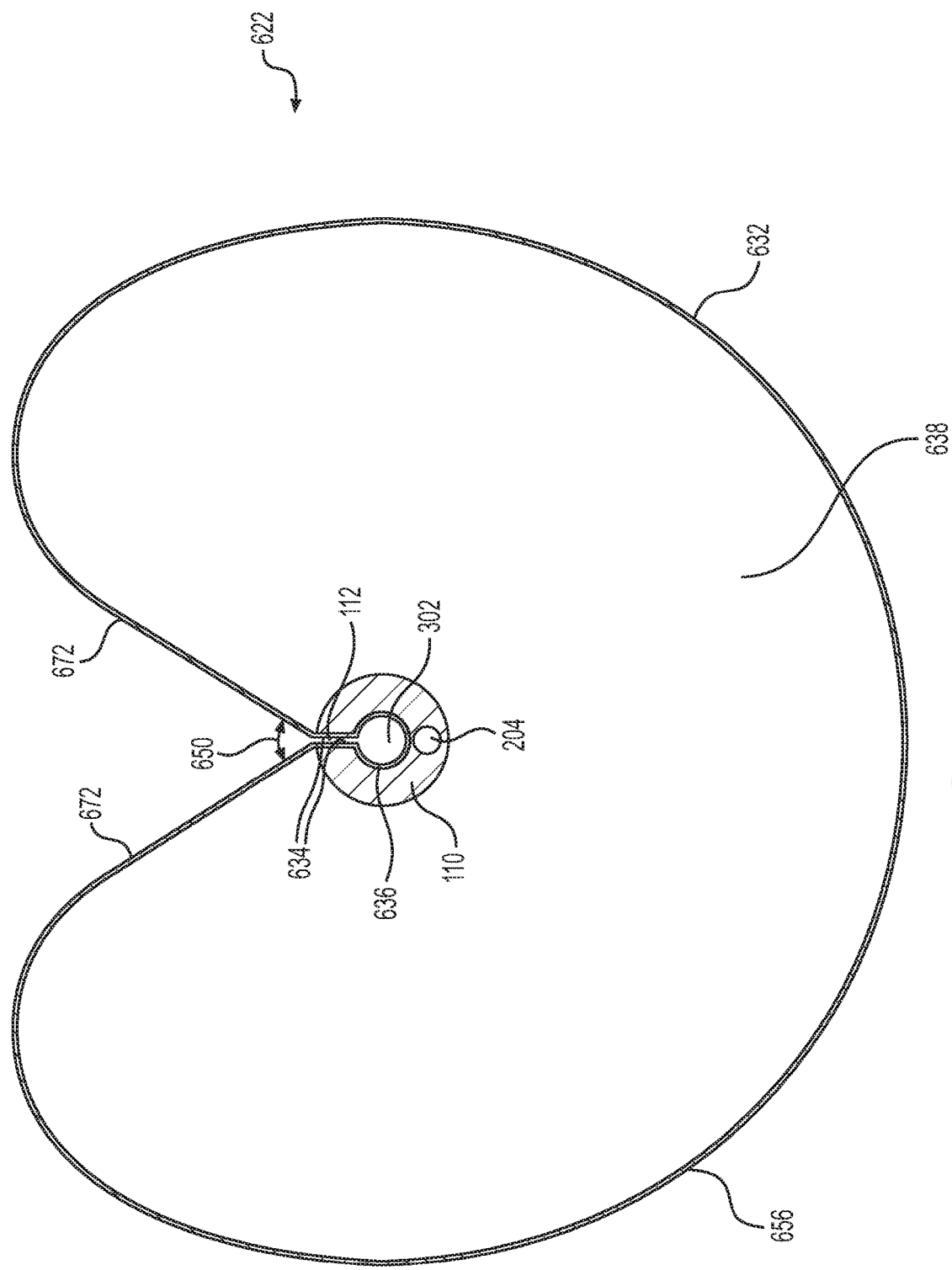

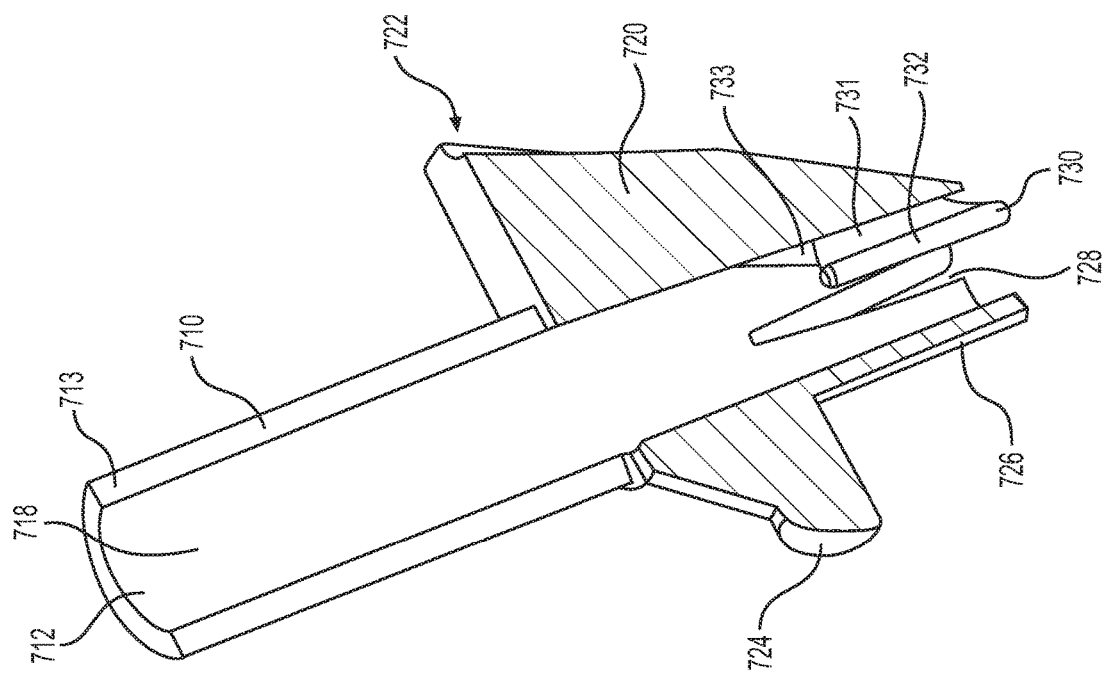
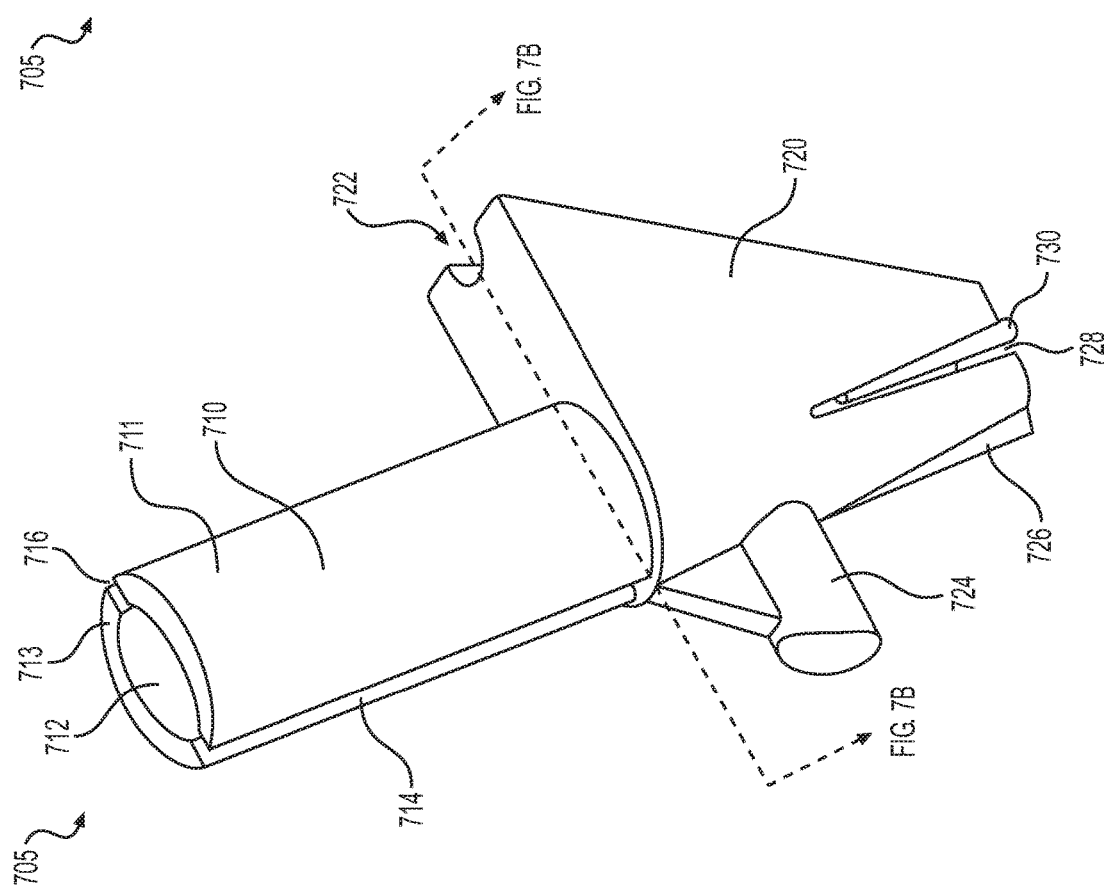

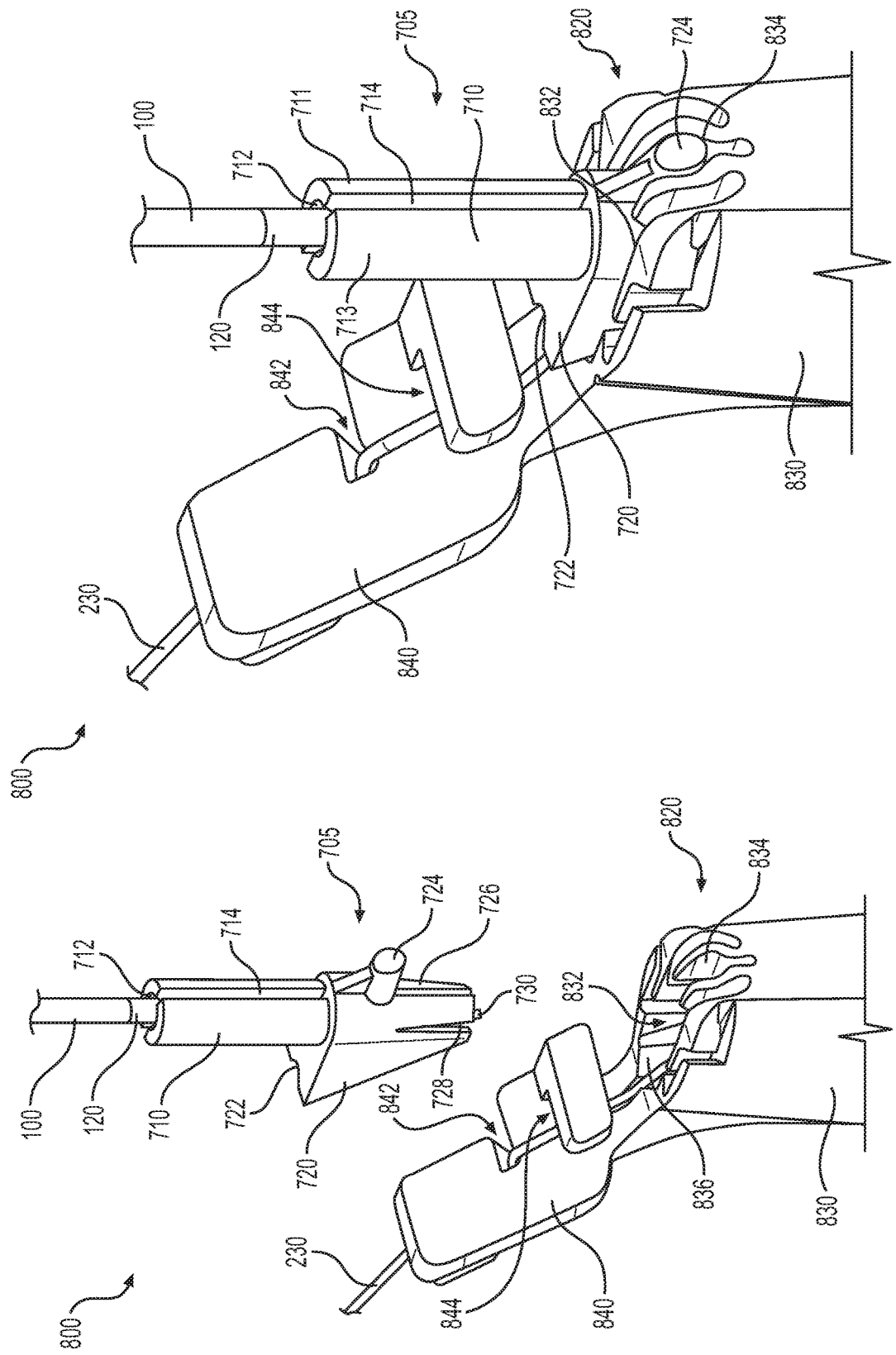

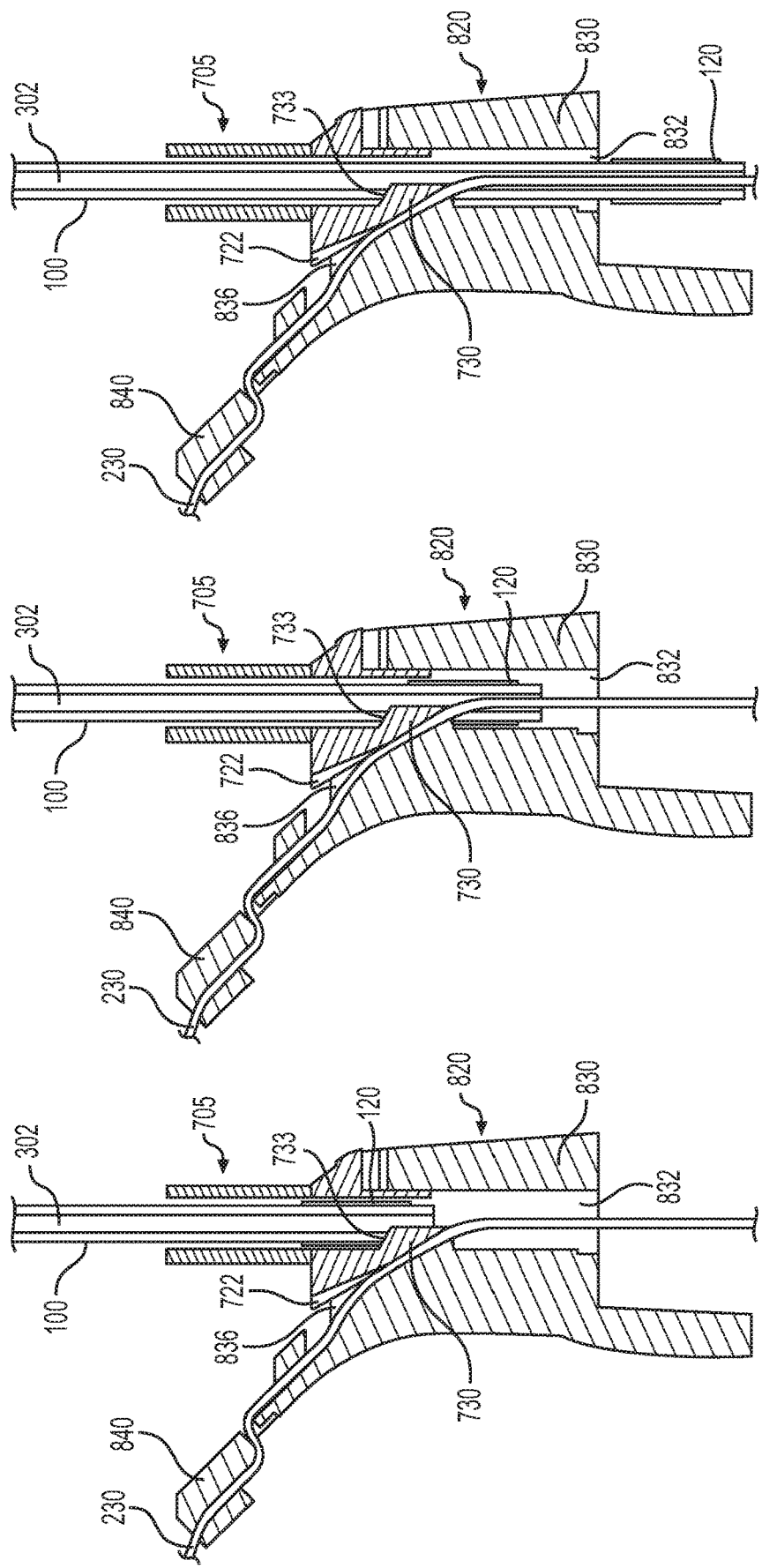

ENDOSCOPIC BALLOON CATHETER

BACKGROUND

Technical Field

The present disclosure generally relates to endoscopic balloon catheters and methods of use. More particularly, and without limitation, the disclosed embodiments relate to apparatuses, systems, and methods for merging a balloon catheter onto a guidewire during an endoscopic procedure.

Background Description

Balloon catheters are commonly used in a variety of endoscopic procedures. For example, in an endoscopic retrograde cholangiopancreatography (ERCP) procedure, a balloon catheter may be introduced over a guidewire through the working channel of a duodenosope into the biliary tree. The balloon may then be inflated and utilized for one or more operations, such as the removal of a stone or opening of a stricture.

Prior to delivery of the balloon catheter, access to the treatment site must first be established to achieve placement of the guidewire. Often, a first device such as a cannula or a sphincterotome is introduced through the ampullary orifice (papilla of Vater) and into the biliary tree until the distal end of the first device is proximate to a desired site in the biliary tree. A guidewire is introduced to the treatment site with the first device, and is typically held in place in the endoscope when the first device is removed so that access to the treatment site is maintained. Subsequent devices, such as a balloon catheter, may then be introduced over the guidewire and delivered to the treatment site.

Currently, techniques for delivering balloon catheters over guidewires provide the physician limited control of the guidewire. Often, the proximal end of the guidewire must be unlocked from the endoscope and the distal tip of the balloon catheter threaded over the proximal end of the guidewire. The balloon catheter is then delivered over the guidewire to the treatment site and the proximal end of the guidewire re-locked to the endoscope. This unlocking and re-locking of the guidewire can result in movement or displacement of the distal end of the guidewire and thus loss of access to the treatment site. Additionally, this process is time- and energy-consuming for the physician or practitioner.

Therefore, an improved apparatus or system is needed which allows delivery of a balloon catheter over a guidewire which remains fixed or locked in a desired position during an endoscopic procedure. Such an apparatus or system may be capable of maintaining access to the treatment site during delivery of the balloon catheter, and may be capable of reducing the time needed for the physician or practitioner to perform the endoscopic procedure, thus increasing the effectiveness of the procedure.

SUMMARY

The embodiments of the present disclosure include apparatuses, systems, and methods for an endoscopic balloon catheter. Advantageously, the exemplary embodiments provide a balloon catheter which is easily introduced onto a fixed or locked guidewire for delivery of the balloon catheter to a treatment site over the guidewire during an endoscopic procedure.

According to an exemplary embodiment of the present disclosure, a balloon catheter for medical procedure is described. The catheter includes a flexible, elongated catheter body. The catheter body includes an inflation lumen and a guidewire lumen configured to receive a guidewire therein. The catheter additionally includes an inflatable balloon affixed to the catheter body. The catheter further includes a slit. The slit extends from a distal end of the guidewire lumen along at least a portion of the length of the guidewire lumen to a position proximal of the balloon.

According to a further exemplary embodiment of the present disclosure, an apparatus for removable engagement with a guidewire is described. The apparatus includes a catheter. The catheter includes a flexible, elongated catheter body. The catheter body includes an inflation lumen and a guidewire lumen. The catheter additionally includes an inflatable balloon affixed to the catheter body. The catheter further includes a slit. The slit extends from a distal end of the guidewire lumen along at least a portion of the length of the guidewire lumen to a position proximal of the balloon. The apparatus additional includes an adapter configured to merge the catheter onto a guidewire. The adapter includes an adapter lumen and a wedge. The adapter lumen is configured to receive the catheter body and the balloon. The wedge extends from an inner surface of the adapter lumen. The wedge is configured to widen a portion of the slit such that a portion of the guidewire merges into the catheter body through the widened portion of the slit.

According to a yet further exemplary embodiment of the present disclosure, a method for merging a balloon catheter onto a guidewire is described. The method includes obtaining a catheter. The catheter includes a flexible, elongated catheter body. The catheter body includes an inflation lumen and a guidewire lumen. The catheter additionally includes an inflatable balloon affixed to the catheter body. The catheter further includes a slit. The slit extends from a distal end of the guidewire lumen along at least a portion of the length of the guidewire lumen to a position proximal of the balloon. The method additionally includes obtaining an adapter configured to merge the catheter onto a guidewire. The adapter includes an adapter lumen and a wedge. The adapter lumen is configured to receive the catheter body and the balloon. The wedge extends from an inner surface of the adapter lumen. The method further includes receiving the catheter within the adapter lumen of the adapter such that the wedge engages and widens a portion of the slit. The method still further includes merging a portion of a guidewire into the catheter through the widened portion of the slit.

According to a still further exemplary embodiment of the present disclosure, an adapter for merging a catheter onto a guidewire is described. The adapter includes means for receiving a catheter having an inflatable balloon affixed thereto. The catheter includes a slit which extends along at least a portion of the length of the catheter to a position proximal of the balloon. The adapter additionally includes means for widening a portion of the slit of the catheter such that a portion of the guidewire merges into the catheter through the widened portion of the slit.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

FIG. 4D is an end view of the exemplary balloon catheter of FIG. 4C as viewed in the proximal direction, according to embodiments of the present disclosure.

FIG. 6D is a cross-sectional view of the exemplary balloon catheter of FIG. 6C as viewed in a proximal direction, according to embodiments of the present disclosure.

FIG. 7A is a perspective view of an exemplary adapter, according to embodiments of the present disclosure.

FIG. 7B is a cross-sectional view of the exemplary adapter of FIG. 7A, according to embodiments of the present disclosure.

FIG. 8A is a component view of an exemplary balloon catheter exchange system, according to embodiments of the present disclosure.

FIG. 8B is a perspective view of the exemplary system of FIG. 8A, according to embodiments of the present disclosure.

FIG. 9A-9C depict perpendicular cross-sectional views of the exemplary system of FIG. 8A at different stages of merging an exemplary balloon catheter onto an exemplary guidewire, according to embodiments of the present disclosure.

DETAILED DESCRIPTION

Figure 1A:
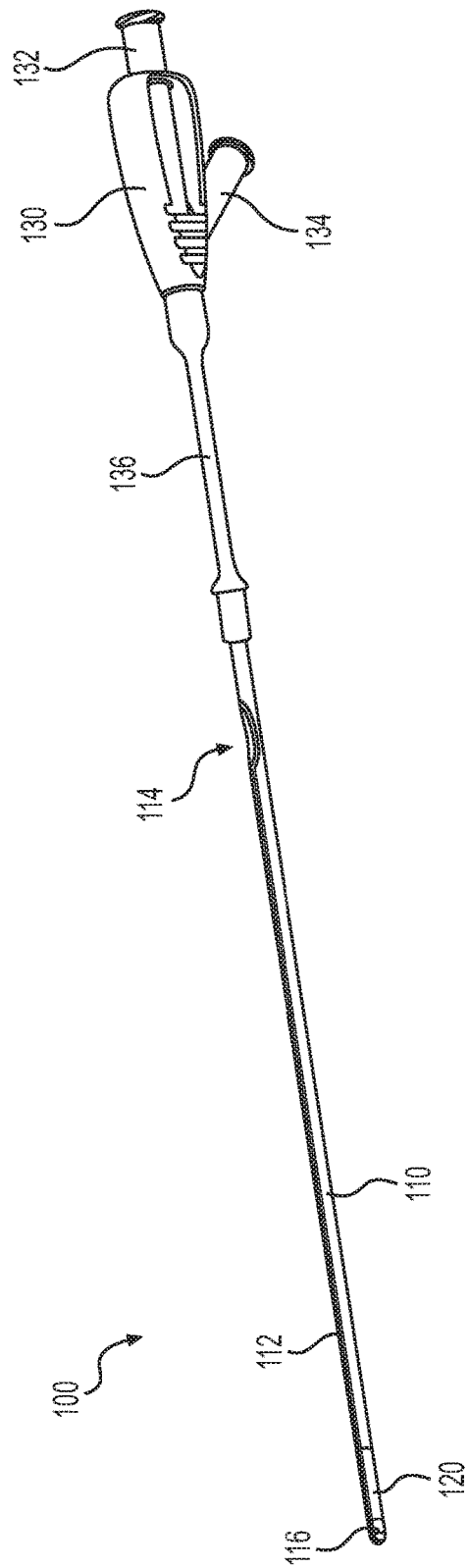
FIG. 1A is a perspective view of an exemplary balloon catheter, according to embodiments of the present disclosure.

Various disclosed embodiments relate to apparatuses, systems, and methods for improved delivery of a balloon catheter onto a guidewire. Various embodiments of the present disclosure may be implemented in an endoscopic system for performing suitable diagnostic and/or therapeutic operations within one or more desired sites in a patient's anatomy. However, it will be appreciated that embodiments of the present disclosure are not limited to endoscopic applications, and that apparatus, systems, and methods disclosed herein may be implemented within any suitable diagnostic and/or therapeutic system. Advantageously, various embodiments of the present disclosure may permit merging of a balloon catheter onto a fixed or locked guidewire, thereby maintaining access to at least one desired treatment site.

As described herein, an endoscope typically includes a proximal end and a distal end, and has one or more internal lumens extending between the distal end and the proximal end. A proximal end may refer to a point or a location along the length of the endoscope closer to a physician or a medical practitioner. A distal end may refer to a point or location along the length of the endoscope closer to a diagnosis or treatment site in the body of a patient during an endoscopic procedure. One of the internal lumens of the endoscope may serve as a working channel. One or more tools may be introduced into the working channel from the proximal end of the endoscope to the distal end of the endoscope until a distal end of the tool approximates or reaches a desired diagnosis or treatment site. As described herein, the longitudinal axis of a channel or elongated device may refer to a central axis or an off-center axis of the channel or tubular structure.

Exemplary endoscopic tools may include balloon catheters. A balloon catheter may be a tubular structure with an inflatable balloon affixed to a distal end thereof. Exemplary balloon catheters according to the present disclosure may be configured for a variety of procedures including, and not limited to, removal of stones or other bodies and dilation of tubular body structures.

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used herein and in the appended claims, the singular forms "a," "an," and "the" include plural references unless the context clearly dictates otherwise.

FIG. 1A is a perspective view of an exemplary balloon catheter 100. Catheter 100 may include catheter body 110, with balloon 120 affixed to a distal portion thereof. Catheter body 110 may be a tubular structure having one or more lumens extending therethrough, including a guidewire lumen, an injection lumen, and an inflation lumen. Balloon 120 may be configured to be inflated and deflated between a deflated state and one or more inflated states. A portion of catheter body 110 may extend distally beyond balloon 120, with distal tip 116 at the distal end of catheter body 110. According to some embodiments, distal tip 116 may be a rounded, atraumatic tip. Catheter body 110 may additionally include skive 114. Skive 114 may be a scalloped cut in catheter body 110 and may be formed using known methods. Skive 114 may extend through the wall of catheter body 110 to reach the guidewire lumen of the catheter body 110. Thus, a guidewire situated within the guidewire lumen may emerge through skive 114. In some embodiments, skive 114 may be positioned in a medial portion of catheter body 110. However, one of ordinary skill in the art will understand that skive 114 may be positioned at any desired portion of catheter body 110 between balloon 120 and hub 130.

Catheter body 110 may additionally include slit 112. Slit 112 may extend longitudinally between distal tip 116 and skive 114, including along the portion of catheter body 110 to which balloon 120 is affixed. Slit 112 may have a natural width, which is the width of slit 112 when it is not stretched or flexed. The natural width of slit 112 may be substantially smaller than the diameter of the guidewire lumen of catheter body 110.

The proximal end of catheter body 110 may extend into and may be secured within hub 130. Catheter body 110 may optionally include strain relief 136, which may be configured to support the joint between catheter body 110 and hub 130. Hub 130 may include one or more of injection port 134 and air port 132. Injection port 134 may be fluidly connected to the injection lumen of catheter body 110. An injection device, such as a syringe, may be connected to injection port 134 to deliver fluid to and/or to withdraw fluid from the treatment site via the injection lumen. Air port 132 may be fluidly connected to the inflation lumen of catheter body 110, which may extend to an inflation opening in catheter body 110. An air supply device may be connected to air port 132 to deliver inflation air into the inflation lumen, which may deliver the air to inflate balloon 120. The air supply device may also deflate balloon 120 by removing air from balloon 120 via the inflation lumen.

Figure 1B:
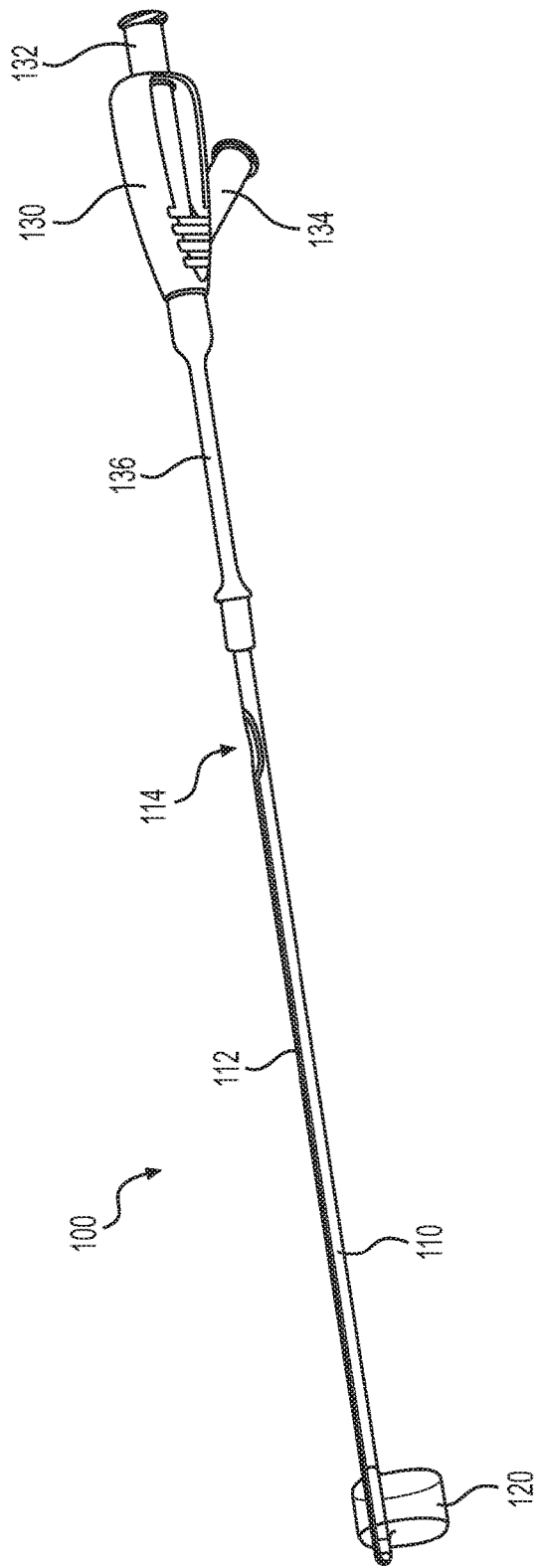
FIG. 1B is a perspective view of the exemplary balloon catheter of FIG. 1A with a balloon in an inflated state, according to embodiments of the present disclosure.

FIG. 1B is a perspective view of the exemplary balloon catheter 100 with balloon 120 in the inflated state. In some embodiments, the size of balloon 120 when in an inflated state may be controlled, at least in part, by the amount of air contained therein. In some embodiments, balloon 120 may be inflated to its full inflation capacity. In other embodiments, balloon 120 may be partially inflated (i.e. inflated to a state between the deflated state and the balloon's full inflation capacity).

Balloon 120 may be formed of one or more layers of compliant material such as polyblend, chronoprene, latex, and polyurethane. Balloon 120 may be bonded to catheter body 110, forming an inflatable chamber. Balloon 120 may be bonded to catheter body 110 by adhesive, heat bonding, laser welding, RF welding, or by other known techniques. According to various embodiments, balloon 120 may assume the deflated state while catheter 100 is delivered to a treatment site through the working channel of an endoscope. For example, catheter 100 may be delivered over a guidewire which extends through the working channel of the endoscope. Once catheter 100 is positioned at the desired treatment site, balloon 120 may be inflated by an air supply device connected to air port 132. The inflated balloon 120 may be utilized to perform a variety of therapeutic procedures, including and not limited to dilation of tubular body structures and removal of bodies such as gallstones. Balloon 120 may then be deflated and catheter 100 removed.

Figure 1C:
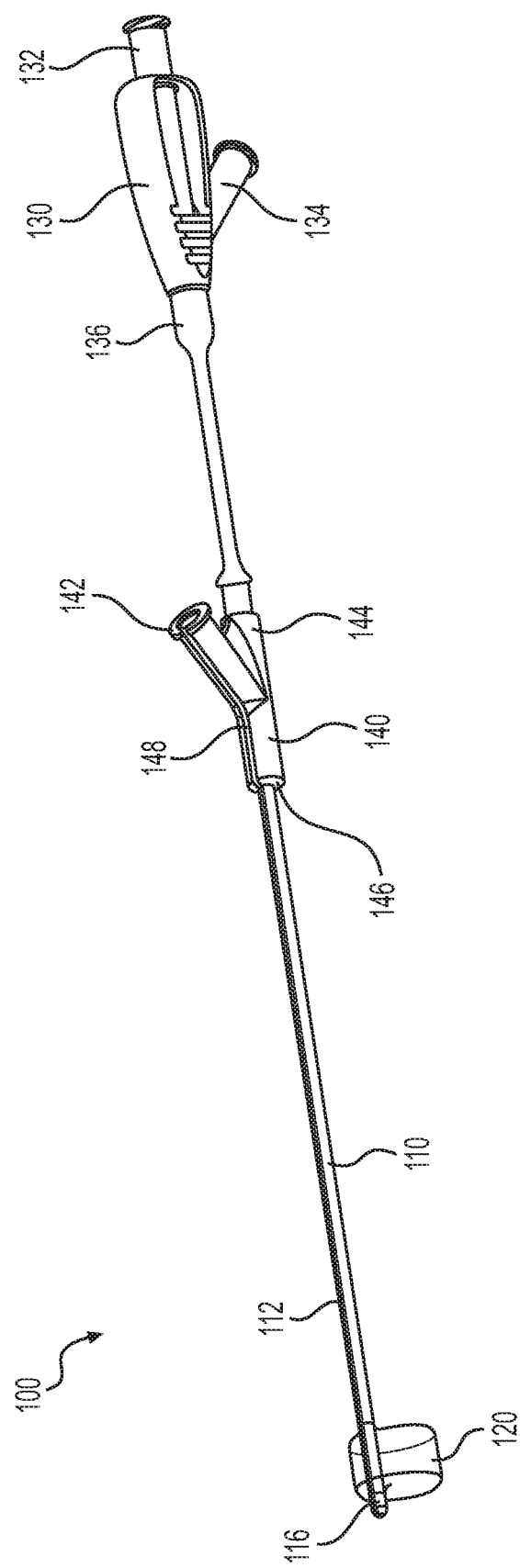
FIG. 1C is a perspective view of the exemplary balloon catheter of FIG. 1B with an exemplary guidewire port, according to embodiments of the present disclosure.

FIG. 1C is a perspective view of exemplary balloon catheter 100. Balloon catheter 100 may optionally include guidewire port 140 arranged about skive 114. According to some embodiments, guidewire port 140 may be removable from catheter body 110 according to the user's preference. Guidewire port 140 may include proximal opening 144 and distal opening 146 through which catheter body 110 may pass. Guidewire port 140 may additionally include guidewire inlet 142, through which a guidewire may be introduced to pass through skive 114 and into the guidewire lumen of catheter body 110. Guidewire port 140 may also include guidewire port slit 148. Port slit 148 may extend between distal opening 146 and guidewire inlet 142. Port slit 148 may be aligned with slit 112 such that they are coaxial. In some embodiments, the width of slit 148 may be larger than the diameter of a guidewire to be introduced into the guidewire lumen of catheter body 110. As a result, a portion of the guidewire may be passed through port slit 148. In some embodiments, the width of slit 148 may be larger than the natural width of slit 112.

Figure 1D:
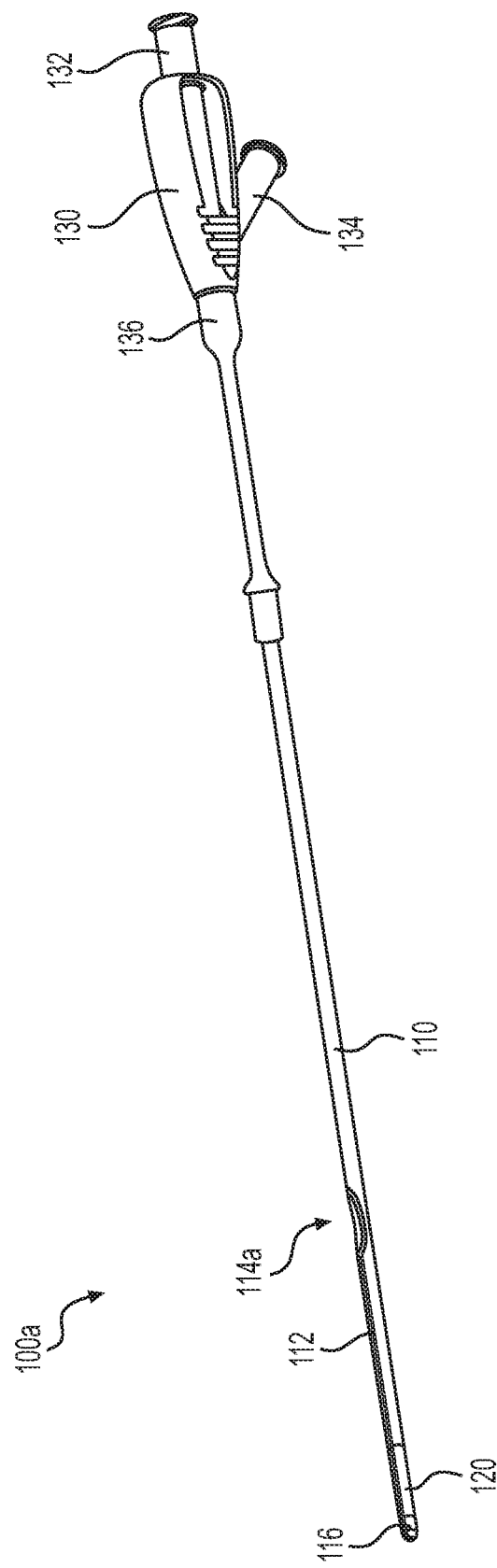
FIG. 1D is a perspective view of an exemplary balloon catheter with a skive positioned in a distal portion thereof, according to embodiments of the present disclosure.

FIG. 1D is a perspective view of another exemplary balloon catheter 100a. Skive 114a of catheter 100a may be situated in a distal region of catheter body —110, closer to tip 116 than to hub 130. Slit 112 may extend longitudinally between tip 116 and skive 114a. According to various embodiments, a guidewire may be situated within the guidewire lumen of catheter 100a, exiting catheter 100a at distal tip 116 and at skive 114. The portion of the guidewire which exits catheter 100a at skive 114a may extend parallel to catheter body 110 until it reaches a proximal end thereof.

Figure 2A:
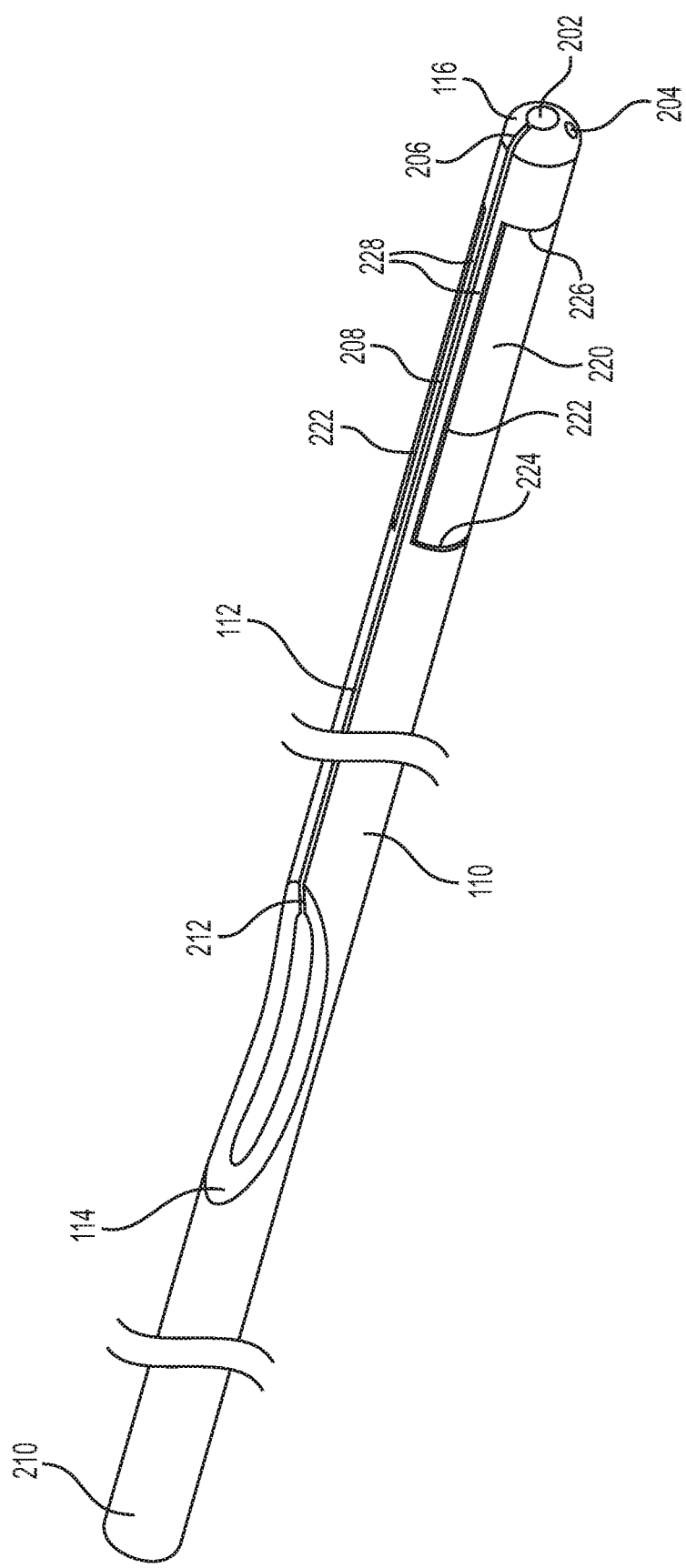
FIG. 2A is a perspective view of an exemplary catheter body of the exemplary balloon catheter of FIG. 1A, according to embodiments of the present disclosure.
Figure 2B:
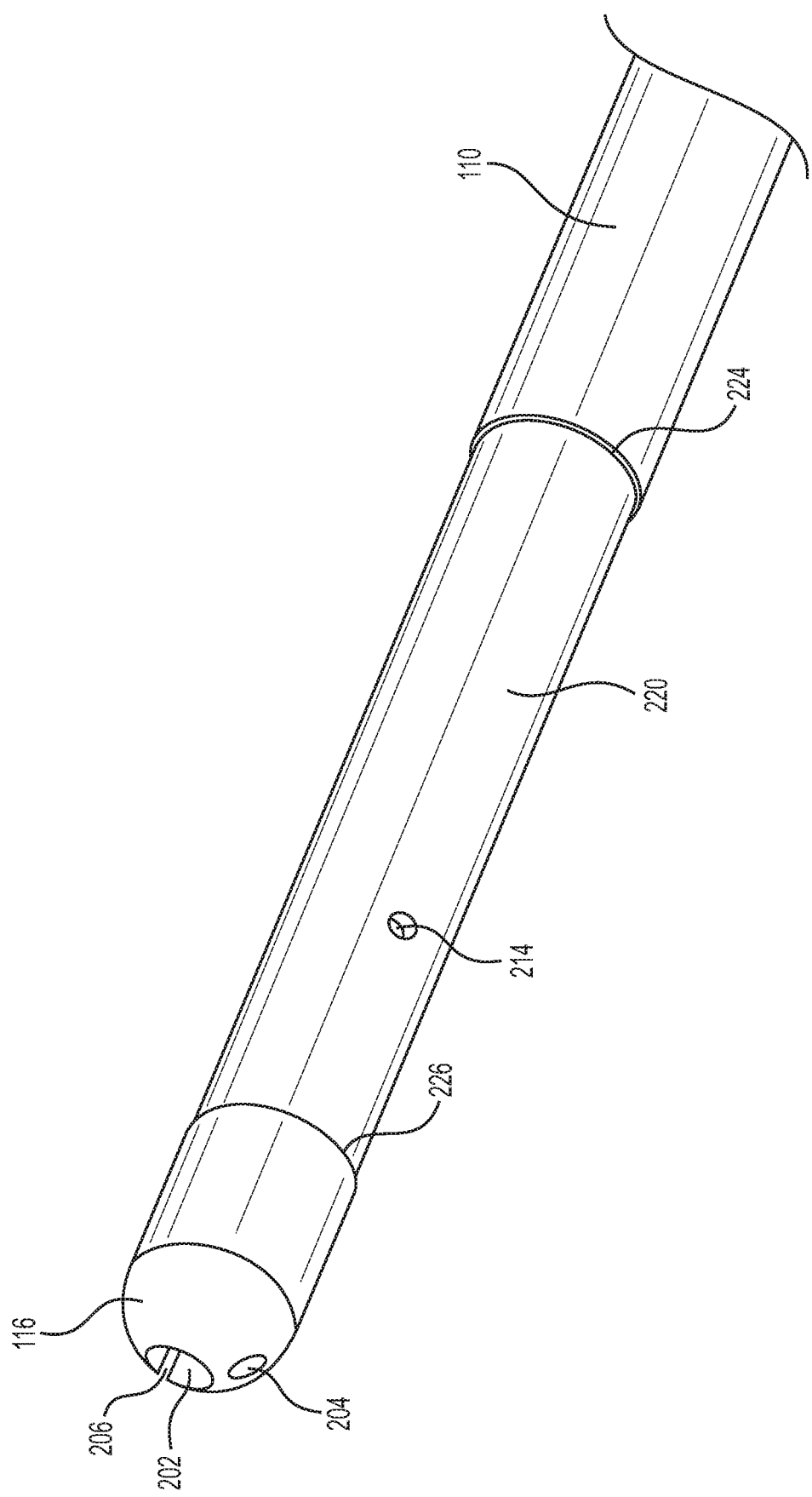
FIG. 2B is a perspective view of the exemplary catheter body of FIG. 2A, according to embodiments of the present disclosure.
Figure 2C:
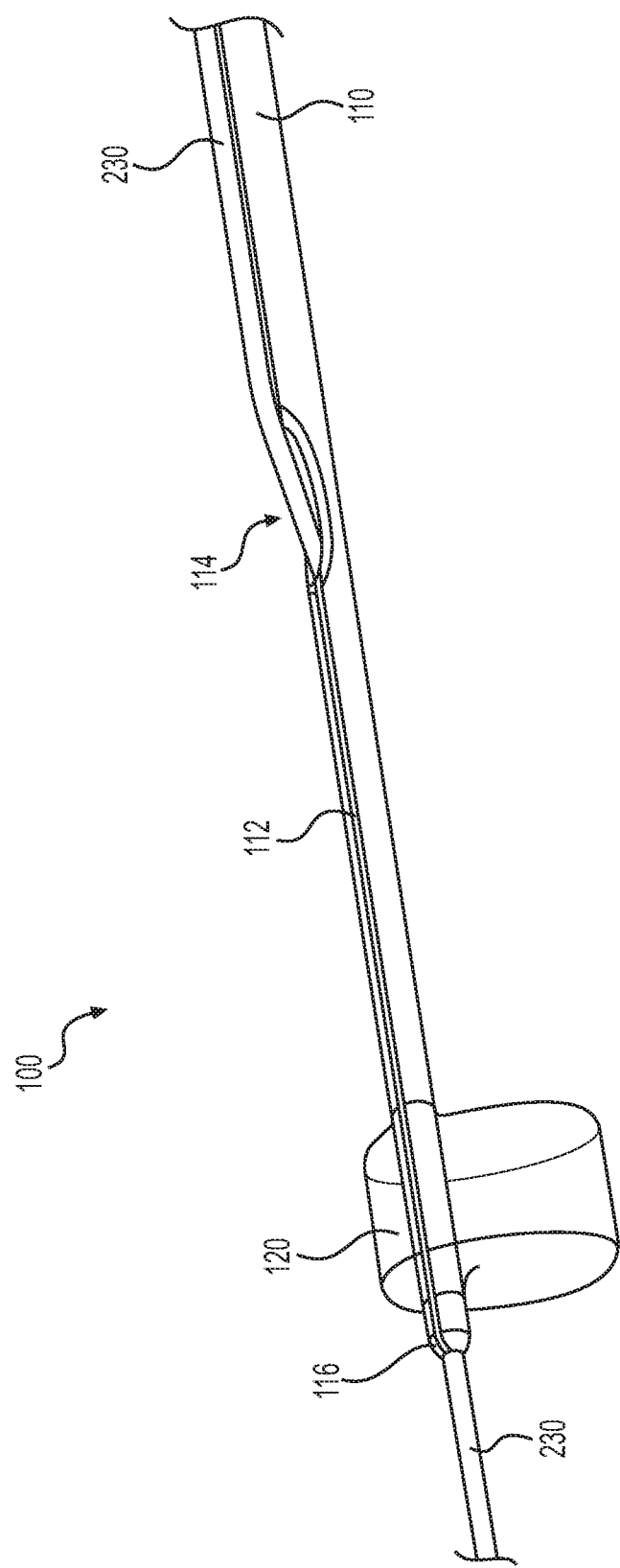
FIG. 2C is a perspective view of the exemplary catheter body of FIG. 2A with a guidewire inserted therein, according to embodiments of the present disclosure.

FIG. 2A is a perspective view of catheter body 110, in which the top of catheter body 110 may be viewed. FIG. 2B is another perspective view of catheter body 110, in which the bottom of catheter body 110 may be viewed. FIG. 2C is a further perspective view of catheter body 110, into a portion of which guidewire 230 has been inserted. The views of FIG. 2A and FIG. 2B depict catheter body 110 without balloon 120 arranged thereon.

Catheter body 110 may include guidewire lumen 202, inflation lumen 214, and injection lumen 204. Guidewire lumen 202 may extend between the distal tip 116 of the catheter body and skive 114, and may be configured to receive an exemplary guidewire 230 therein. Slit 112 may extend radially between guidewire lumen 202 and the outer surface of catheter body 110. In some embodiments, guidewire lumen 202 may have an inner diameter which is larger than the outer diameter of exemplary guidewire 230, such that guidewire 230 may easily slide within guidewire lumen 202. According to some embodiments, guidewire lumen 202 may be lubricated to reduce friction between guidewire 230 and the wall of guidewire lumen 202. Inflation lumen 214 may extend between proximal end 210 of the catheter body and an inflation opening, and may supply air to and withdraw air from balloon 120. The proximal end of inflation lumen 214 may be fluidly connected to air port 132. Injection lumen 204 may extend longitudinally along at least a portion of catheter body 110 and may deliver fluids to and/or withdraw fluids from a treatment site. The proximal end of injection lumen 204 may be fluidly connected to injection port 134.

Distal tip 116 of catheter body 110 may include a number of distal openings of the various lumens extending along catheter body 110. For example, distal tip 116 may include a distal opening of guidewire lumen 202 and a distal opening of injection lumen 204. Guidewire lumen 202 may extend longitudinally between distal tip 116 and skive 114, with skive 114 forming the proximal end of guidewire lumen 202. In some embodiments, guidewire lumen 202 may be configured to receive an exemplary guidewire which is substantially greater in length than guidewire lumen 202, for example guidewire 230. The guidewire 230 may extend along the entire length of guidewire lumen 202, and may extend out through the distal opening of guidewire lumen 202 and through skive 114. Catheter 100 may be introduced to a desired treatment site via guidewire 230 by the passage of guidewire lumen 202 over guidewire 230. In some embodiments, guidewire lumen 202 may be positioned in the center of distal tip 116. In other embodiments, guidewire lumen 202 may be positioned radially outward from the center of distal tip 116.

Injection lumen 204 may extend from proximal end 210 of the catheter body 110 to at least one opening, such as an opening on or near distal tip 116. In some embodiments, catheter body 110 may include a plurality of distal outlets of injection lumen 204. Injection lumen 204 may be fluidly connected to injection port 134. In some embodiments, injection lumen 204 may be utilized to deliver therapeutic, rinsing, or contrast fluids to the treatment site and/or for delivery of a secondary device to the treatment site. Additionally or alternatively, injection lumen 204 may be utilized for the withdrawal of fluids from the treatment site, such as for sampling or for clearing the treatment site. In some openings, an opening of injection lumen 204 may be situated distal to balloon 120. Alternatively or additionally, an opening of injection lumen 204 may be situated proximal of balloon 120

Referring to FIG. 2B, catheter body 110 may additionally include inflation lumen 214. Inflation lumen 214 may extend longitudinally at least to the proximal end of balloon 120, and may include an opening which may extend through a wall of catheter 110 to deliver air to balloon 120 (not pictured in FIG. 2B). As illustrated in FIG. 2B, the opening of inflation lumen 214 may be positioned proximal of distal tip 116 at a position over which balloon 120 is affixed. As a result, air supplied from inflation lumen 214 may pass through the opening and may inflate balloon 120. Further, removal of air through inflation lumen 214 may cause deflation of balloon 120. According to various embodiments in which catheter body 110 includes depression 220, an opening of inflation lumen 214 may be positioned within depression 220.

Slit 112 may extend longitudinally along the length of catheter body 110 between distal tip 116 and skive 114. As a result, slit 112 may extend longitudinally along the entire length of guidewire lumen 202. Distal end 206 of the slit may extend along distal tip 116 and may merge with guidewire lumen 202. The slit may include a portion 208 which extends adjacent to balloon 120. Proximal end 212 of the slit may extend along the scalloped cut of skive 114 and may merge with guidewire lumen 202. According to the embodiment of FIG. 2A, skive 114 may be positioned within a medial portion of catheter body 110.

In some embodiments, catheter body 110 may include depression 220 at the distal portion thereof. Depression 220 may be one or more indentations formed in the outer surface of catheter body 110. Depression 220 may include two axial edges 222 which are parallel to and equidistant from slit 112. Depression 220 may additionally include proximal edge 224 and distal edge 226. Edges 224 and 226 may extend circumferentially about a portion of catheter body 110. In some embodiments, depression 220 may be formed in catheter body 110 by removing material from the outer surface of catheter body 110 by laser ablation, chemical etching, and/or heat ablation. Alternatively, depression 220 may be formed according to other known techniques. Depression 220 may have a constant depth across its entire surface. According to some embodiments, axial edges 222 may extend along slit 112. As a result, depression 220 may extend circumferentially about the entire surface of catheter body 110 which is not occupied by slit 112. According to alternative embodiments, two raised portions 228 may extend between axial edges 222 of the depression and slit 112, the outer surfaces of raised portions 228 being situated radially outwards from the outer surface of depression 220.

A portion or the entirety of balloon 120 may be situated within depression 220. According to some embodiments, the depth of depression 220 may be equal to the thickness of balloon 120. As a result, when balloon 120 is in the deflated state, the outer surface of balloon 120 may be substantially even with the outer surface of catheter body 110, thus providing a constant diameter outer surface of balloon catheter 100. In various alternative embodiments, the outer surface of balloon 120 may be positioned radially inward or radially outward from the outer surface of catheter body 110 when balloon 120 is in the deflated state. In some embodiments, the bonds between balloon 120 and catheter body 110 may be situated within depression 220. Advantageously, this may ensure that bonding material is retained within depression 220 and does not flow into slit 112. Alternatively or additionally, grooves (not pictured in FIG. 2A) may be formed in one or more of catheter body 110 and depression 220, the bonds between balloon 120 and catheter body 110 aligning with and being situated within the grooves. As a result, the outer surface of the bonds may be even with or positioned radially inward from the outer surface of balloon 120. Advantageously, such grooves may give catheter 100 a more pleasing appearance since the bonds may be less noticeable.

Figure 3:
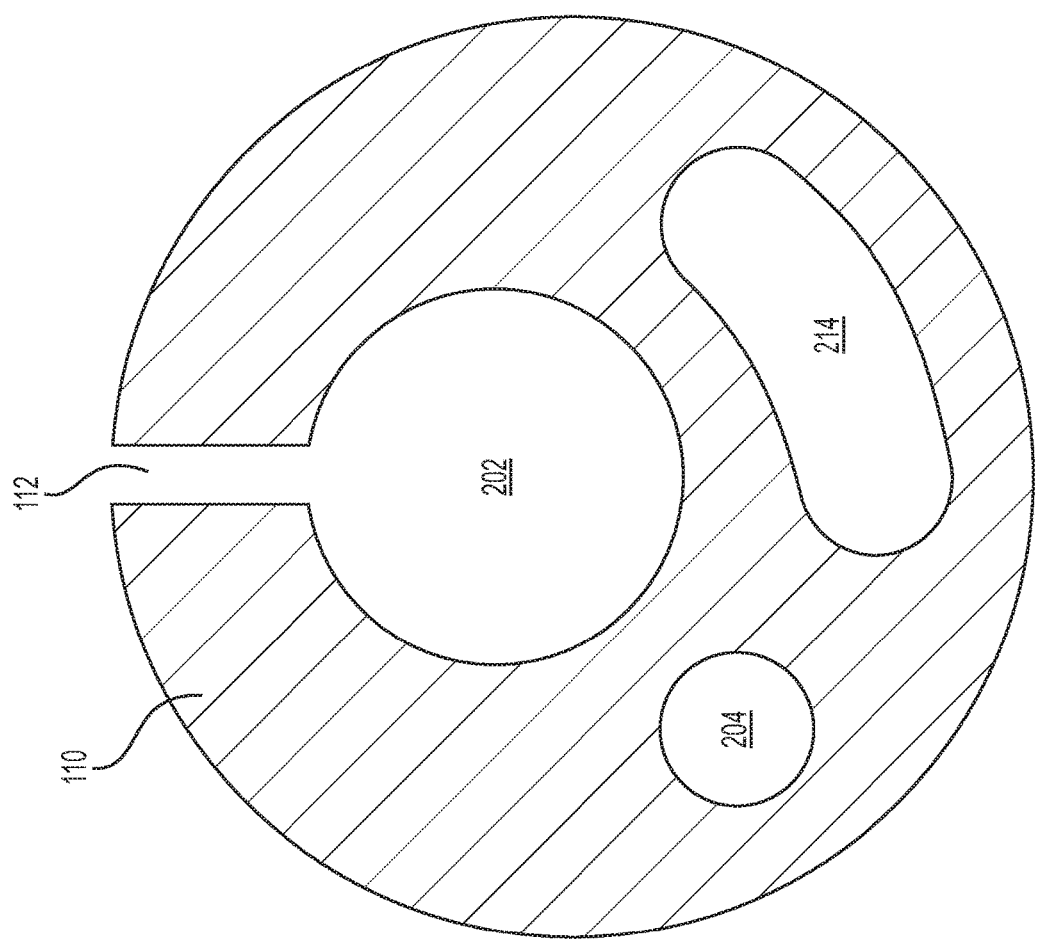
FIG. 3 is a cross-sectional view of the exemplary catheter body of FIG. 2A as viewed in a proximal direction, according to embodiments of the present disclosure.

FIG. 3 is a cross-sectional view of exemplary catheter body 110 as viewed in the proximal direction. Catheter body 110 may include guidewire lumen 202, inflation lumen 214, and injection lumen 204. Catheter body 110 may be constructed of any suitable compliant polymeric material such as PTFE, PEBA, nylon, polyethylene, etc. Due to the elastic nature of catheter body 110, slit 112 may be stretched or widened beyond its natural width. This widening may occur, for example, due to the application of a widening force by a structure positioned within slit 112. Slit 112 may be stretched to a width equal to or greater than the diameter of a guidewire. Slit 112 may re-assume its natural width after the stretching force is removed.

Referring again to FIG. 1A, catheter body 110 may be merged onto a guidewire through slit 112. In some embodiments, a portion of slit 112 may be opened or widened, and a section of the guidewire passed through slit 112 and into guidewire lumen 202. When slit 112 returns to its natural width, the guidewire may be securely retained within guidewire lumen 202 due to the fact that the diameter of the guidewire is substantially larger than the natural width. Due to this merging mechanism, unlike prior endoscopic balloon catheters, exemplary balloon catheters 100 may be merged onto a medial section of a guidewire, instead of onto the proximal tip of the guidewire. Advantageously, this may allow the proximal tip of the guidewire to remain locked or fixed to the endoscope while balloon catheter 100 is merged onto a more distal portion of the guidewire via slit 112. The entire length of guidewire lumen 202 may be merged onto the guidewire, including the portion which is adjacent to balloon 120, after which balloon catheter 100 may be delivered to the treatment site by the guidewire. Additionally, slit 112 may allow balloon catheter 100 to be removed off of the guidewire by being split or separated from the guidewire via slit 112. The proximal end of the guidewire may remained fixed or locked while balloon catheter 100 is removed off of the guidewire. Advantageously, because the proximal end of the guidewire may remain fixed in a locking device during introduction, use, and removal of balloon catheter 100, the physician does not need to unlock the guidewire. Therefore, access to the desired treatment site may be effectively maintained during the endoscopic procedure.

Figure 4A:
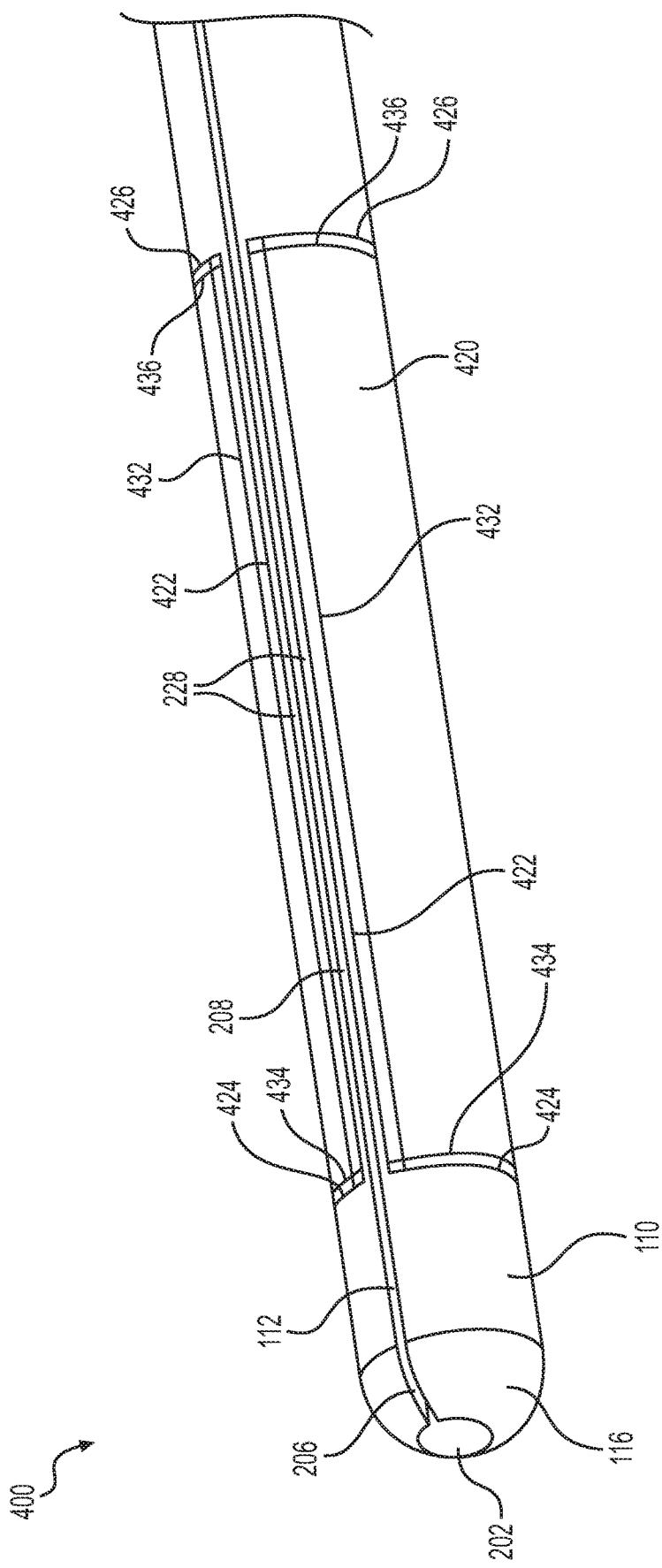
FIG. 4A is a perspective view of a distal portion of an exemplary balloon catheter, according to embodiments of the present disclosure.

FIG. 4A is a perspective view of a distal portion of an exemplary balloon catheter 400, according to various embodiments of the present disclosure. Balloon catheter 400 may include catheter body 110 with balloon 420 positioned on a distal portion thereof. Balloon 420 may be formed of a single layer of compliant material. The single layer may be generally rectangular with two axial edges 422, a distal edge 424, and a proximal edge 426. The single layer may be wrapped circumferentially about catheter body 110 and may be secured thereto along two axial bonds 432, distal bond 434, and proximal bond 436. Bonds 432-436 may be formed using aforementioned bonding techniques. According to some embodiments, bonds 432-436 may be situated along edges 422-426. According to other embodiments, bonds 432-436 may be positioned inwards from edges 422-426, with a small margin between them. Bonds 432-436 may intersect such that they form an air-tight inflatable chamber. As a result, the inflatable chamber of balloon 420 may be formed between balloon 420 and the outer surface of catheter body 110, with the edges of the inflatable chamber secured in an air-tight fashion by bonds 432-436. Axial edges 422 may be parallel to each other and to slit 112, and may be equidistant from slit 112. Portion 208 of the slit may extend between axial edges 422 such that slit 112 does not interrupt or extend into the inflatable chamber of balloon 420.

Figure 4B:
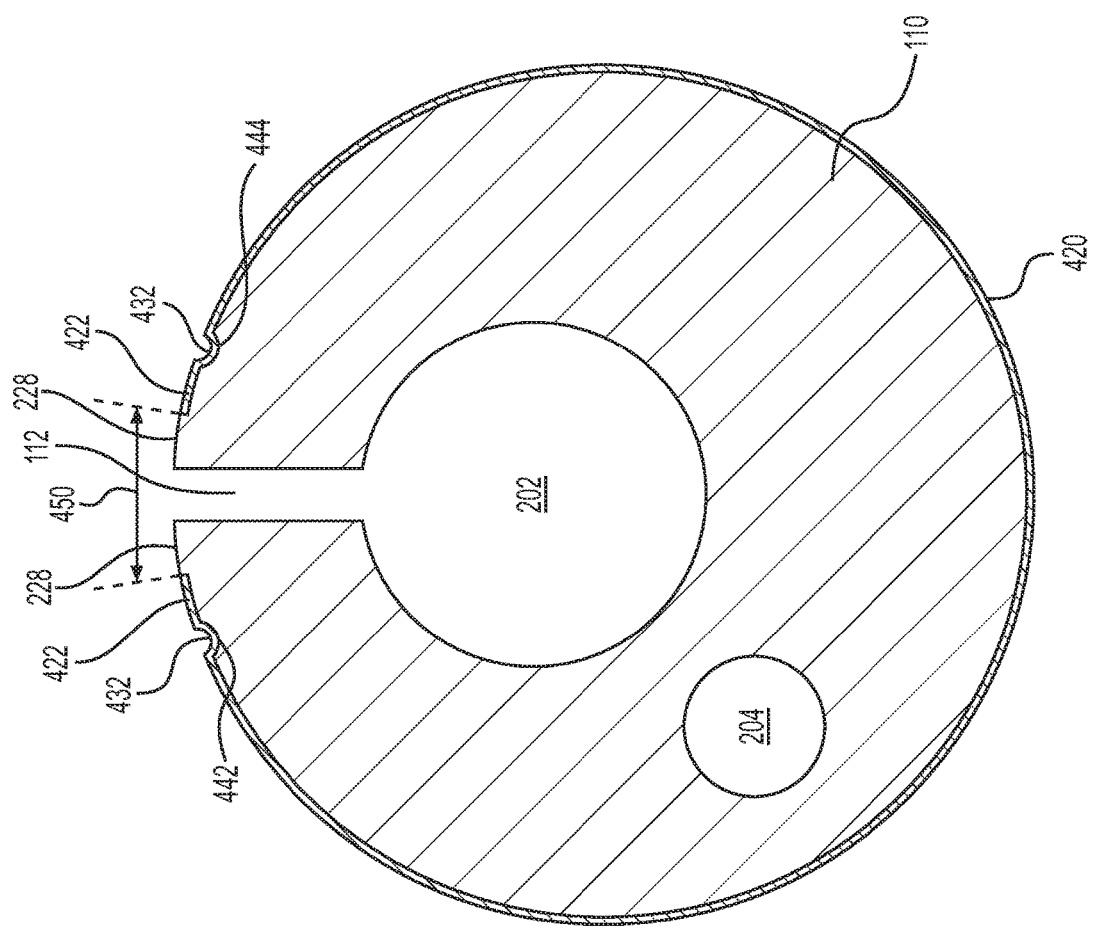
FIG. 4B is a cross-sectional view of the exemplary balloon catheter of FIG. 4A as viewed in a proximal direction, according to embodiments of the present disclosure.

FIG. 4B is a cross-sectional view of balloon catheter 400 as viewed in the proximal direction. FIG. 4B depicts a cross-sectional view of balloon catheter 400 with balloon 420 in the deflated state. Balloon 420 may wrap circumferentially about catheter body 110, with a discontinuity 450 extending between axial edges 422. Optionally, catheter body 110 may include grooves 442 and 444 which may align with and receive bonds 432. Catheter body 110 may include similar grooves which align with and receive bonds 434 and 436. Slit 112 may be radially aligned with discontinuity 450. According to some embodiments, discontinuity 450 may have a greater width than the natural width of slit 112. According to some embodiments, when slit 112 is widened to allow passage of a portion of a guidewire therethrough, discontinuity 450 may also be widened, thus allowing passage of the guidewire through portion 208 of the slit and minimizing risk of damage to balloon 420 by the guidewire.

Figure 4C:
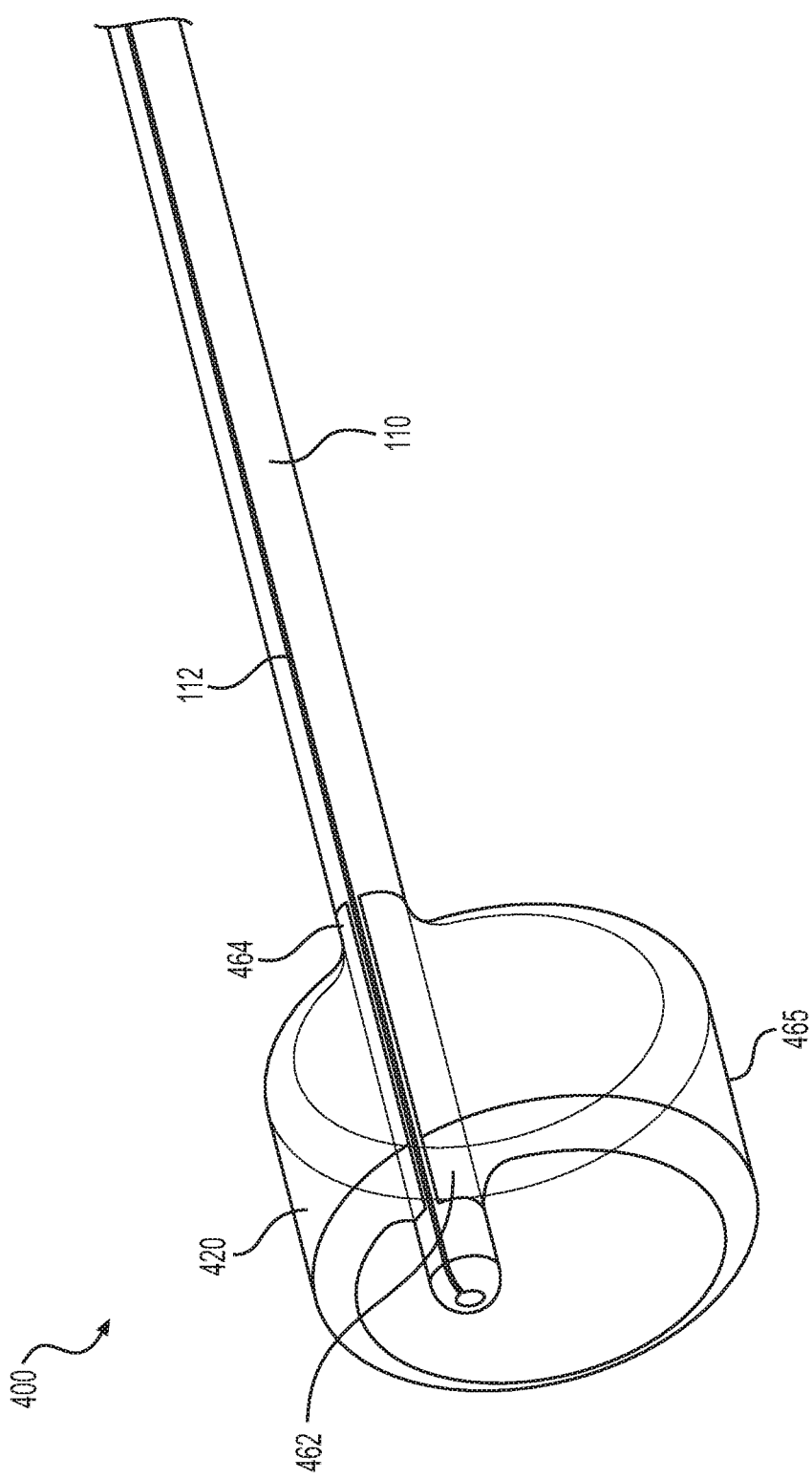
FIG. 4C is a perspective view of the distal portion of the exemplary balloon catheter of FIG. 4A with a balloon in an inflated state, according to embodiments of the present disclosure.

FIG. 4C is a perspective view of the distal portion of balloon catheter 400, with balloon 420 in an inflated configuration. FIG. 4D is an end view thereof as viewed in the proximal direction. In some embodiments, balloon 420 may be constructed of a compliant material. Therefore, an outer surface 465 of balloon 420 may conform to a shape of a body lumen in which catheter 400 may be inserted. Balloon 420 may include reduced diameter portions 462 and 464 at the distal and proximal ends thereof. Portions 462 and 464 may have a smaller diameter than the remainder of balloon 420 when inflated due to their proximity to junctions between axial bonds 432 and proximal and distal bonds 436 and 434. In some embodiments, balloon 420 may be asymmetrical when in the inflated state. For example, when balloon 420 is in the inflated state, catheter body 110 may extend through balloon 420 at a point situated radially outward from the center of balloon 420. This may be due, at least in part, to the fact that balloon 420 does not extend circumferentially around the entire catheter body 110, but is instead interrupted by discontinuity 450.

According to some embodiments, balloon catheter 400 may include a guidewire positioned within guidewire lumen 202. The guidewire may have a diameter which is significantly larger than the natural width of slit 112. Therefore, the guidewire may be securely retained within guidewire lumen 202 when slit 112 exhibits its natural width. The guidewire may be passed between guidewire lumen 202 and an area external to catheter body 110 by widening of slit 112 and passage of the guidewire therethrough.

Figure 5A:
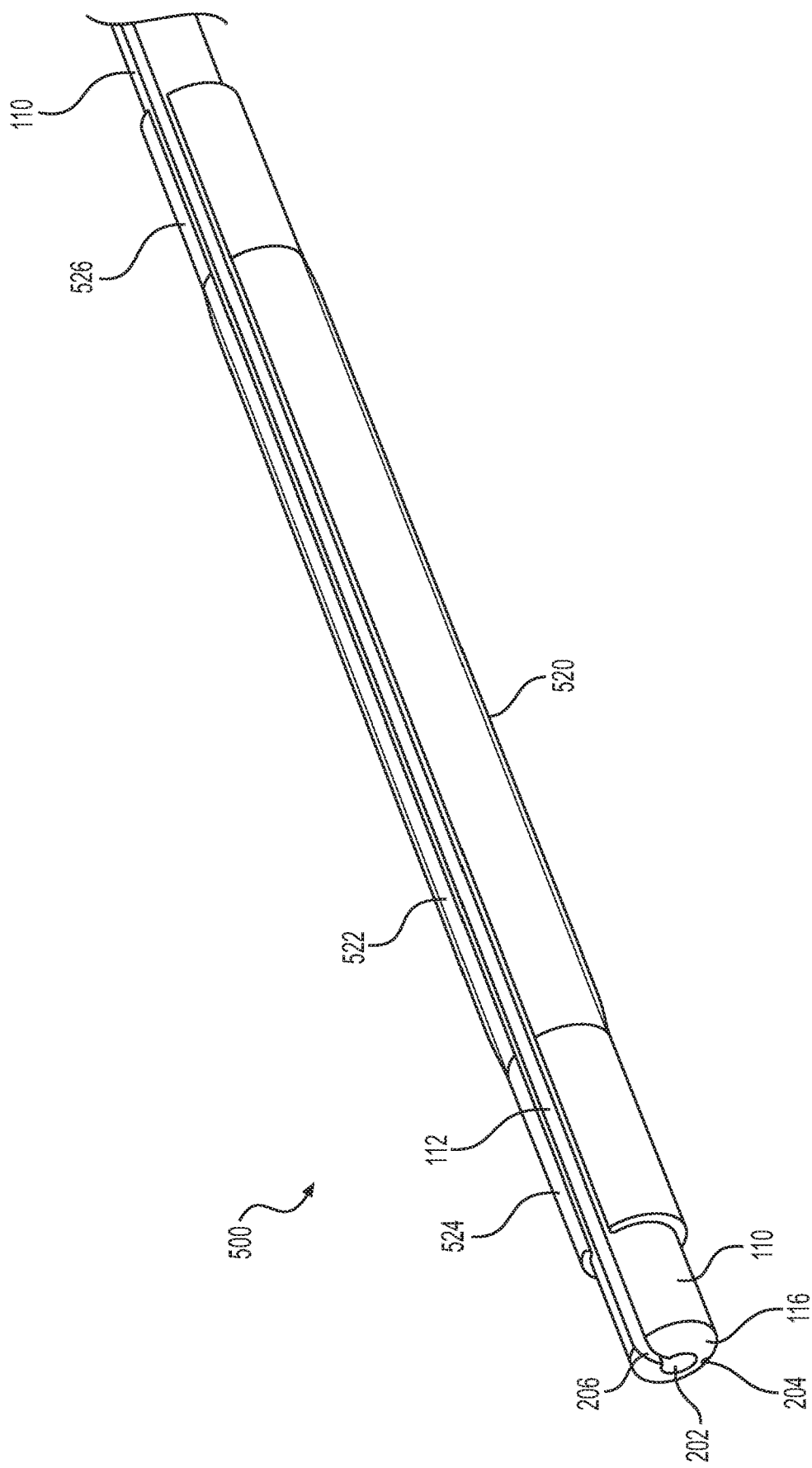
FIG. 5A is a perspective view of a distal portion of another exemplary balloon catheter, according to embodiments of the present disclosure.

FIG. 5A is a perspective view of a distal portion of an exemplary balloon catheter 500, according to various embodiments of the present disclosure. Balloon catheter 500 may include catheter body 110 and balloon 520 affixed to a distal portion thereof. Balloon 520 may be formed by two layers of compliant material and may include inflatable portion 522, distal seal end 524, and proximal seal end 526. Seal ends 524, 526 may include portions of balloon 520 in which the two layers are bonded together by heat bonding, adhesive, RF welding, laser welding, or other known techniques. The bonding of seal ends 524, 526 creates an air-tight seal between them. Inflatable portion 522 may be positioned between seal ends 524, 526 and may be a portion of balloon 520 in which the two layers of compliant material are not bonded together. According to some embodiments, the two layers of compliant material may be formed of a single sheet of compliant material which is folded to form the two layers. According to other embodiments, balloon 520 may be formed by two or more sheets of compliant material which are bonded together by heat bonding, adhesive, RF welding, laser welding, or other known techniques.

Figure 5B:
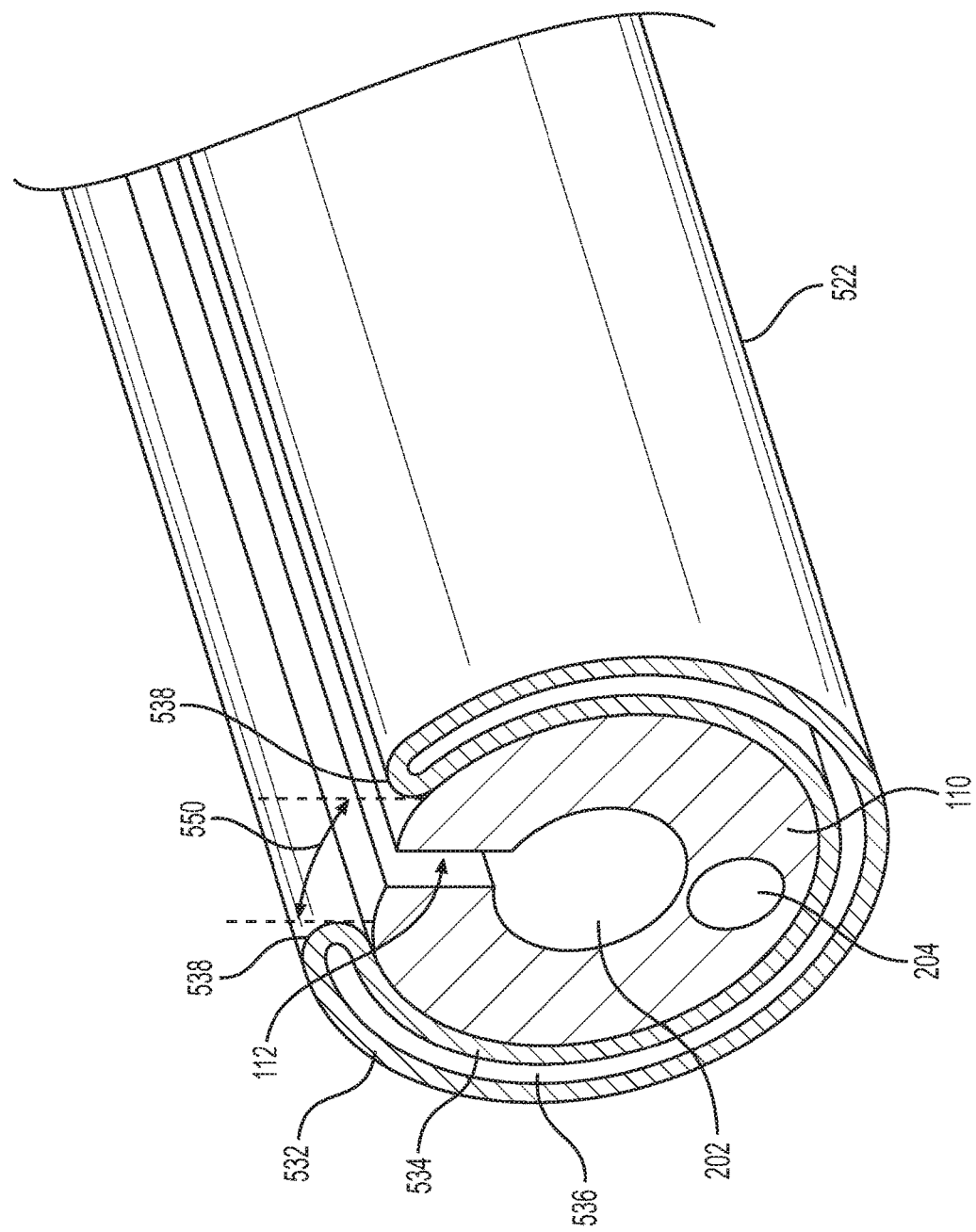
FIG. 5B is a perspective view of a cross-section of the exemplary balloon catheter of FIG. 5A, according to embodiments of the present disclosure.

FIG. 5B is a perspective view of a cross-section of balloon catheter 500, in which balloon 520 is in the deflated state. The two layers of compliant material of balloon 520 may include outer layer 532 and inner layer 534. According to some embodiments, outer layer 532 and inner layer 534 may be equal in thickness. According to other embodiments, inner layer 534 may have a smaller thickness than outer layer 532. As a result, the diameter of balloon 520 may be minimized. An inflatable chamber 536 may be formed between layers 532 and 534. Inflatable chamber 536 may be sealed by seal ends 524, 526 and, according to various embodiments in which the two layers of compliant material include multiple sheets, bonds between the multiple sheets. The inner face of inner layer 534 may be bonded to the outer surface of catheter body 110 using aforementioned techniques. Therefore, balloon 520 may be secured to catheter body 110. According to some embodiments, the entirety of the inner face of inner layer 534 may be bonded to catheter body 110 except for a portion forming an inflation hole (not depicted in FIG. 5B). According to alternative embodiments, sections of the inner face of inner layer 534 may be bonded to catheter body 110.

Balloon 520 may additionally include end portions 538 and 532, which are formed by the junction between inner layer 534 and outer layer 532. A discontinuity 550 may be formed between end portions 538 and 532. Discontinuity 550 may be a circumferential section through which balloon 520 does not extend. Slit 112 may be radially aligned with discontinuity 550. As a result, when a section of the guidewire passes through slit 112, it also passes through discontinuity 550. According to some embodiments, discontinuity 550 may have a greater width than the natural width of slit 112. According to some embodiments, when slit 112 is widened to allow passage of a portion of a guidewire therethrough, discontinuity 550 may also be widened, thus allowing passage of the guidewire through portion 208 of the slit and minimizing risk of damage to balloon 520 by the guidewire. The natural width of slit 112 may be significantly smaller than the diameter of a guidewire placed within guidewire lumen 202. Therefore, the guidewire may be securely retained within guidewire lumen 202 when slit 112 exhibits its natural width. The guidewire may be passed between guidewire lumen 202 and an area external to catheter body 110 by widening of slit 112 and passage of the guidewire therethrough.

Figure 5C:
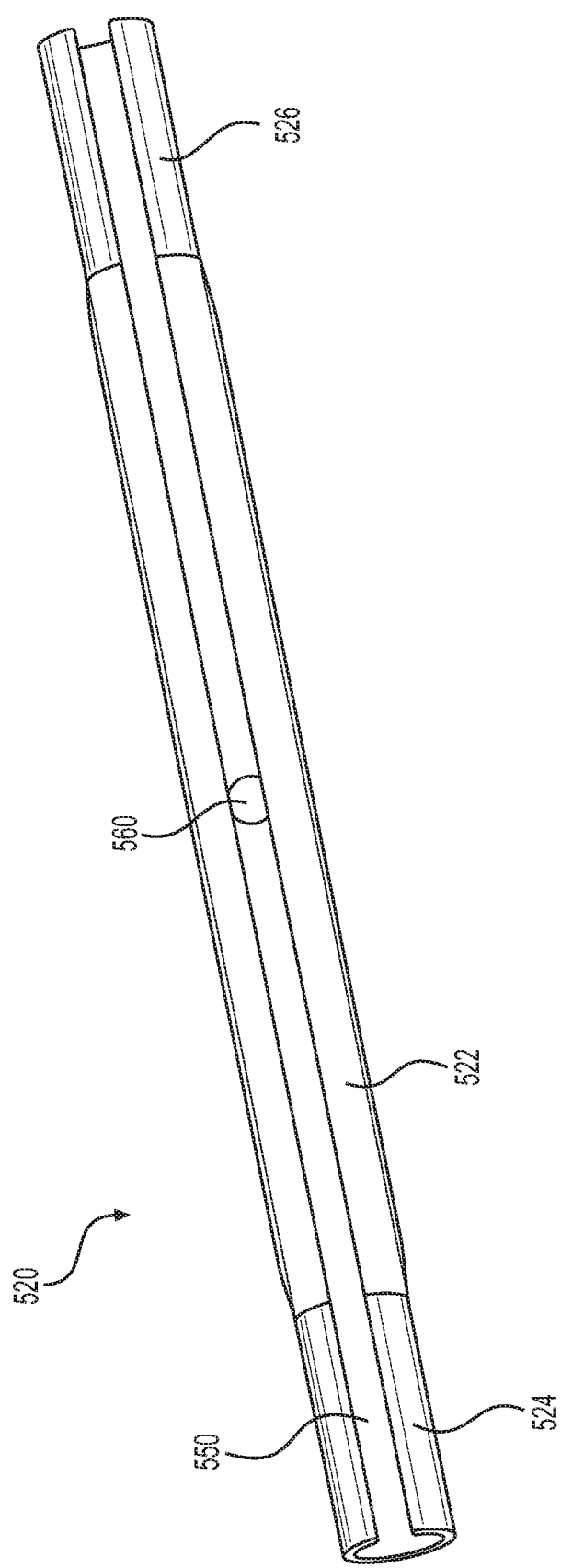
FIG. 5C is a perspective view of a balloon of the exemplary balloon catheter of FIG. 5A, according to embodiments of the present disclosure.

FIG. 5C is a perspective view of balloon 520 in the deflated state, viewed without catheter body 110. According to some embodiments, inflatable portion 522 may have a larger outer diameter than seal ends 524 and 526 due to the fact that layers 532 and 534 are not bonded together in inflatable portion 522. Inner layer 534 may additionally include inflation hole 560. Inflation hole 560 may be aligned with the opening of inflation lumen 214 of catheter body 110 and may supply air to and withdraw air from balloon 520. The air-tight seal of balloon 520 may be maintained by the application of sealant on the portion of inner layer 534 surrounding inflation hole 560, such that air may not pass between inner layer 534 and catheter body 110. The air-tight seal may be reinforced by application of sealant between seal ends 524, 526 and catheter body 110. Discontinuity 550 may extend longitudinally along the length of balloon 520.

Figure 5D:
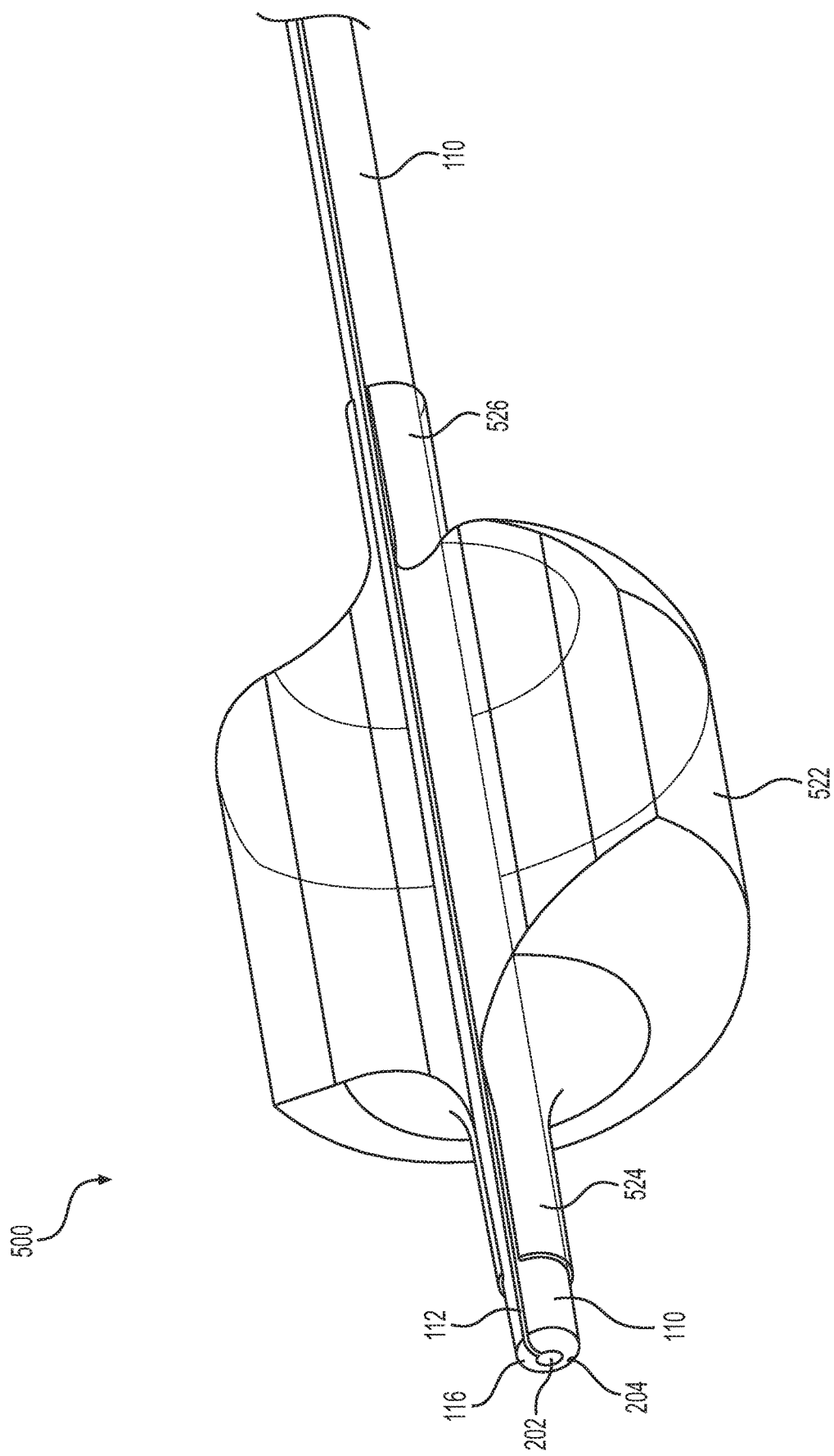
FIG. 5D is a perspective view of the distal portion of the exemplary balloon catheter of FIG. 5A with the balloon in an inflated state, according to embodiments of the present disclosure.
Figure 5E:
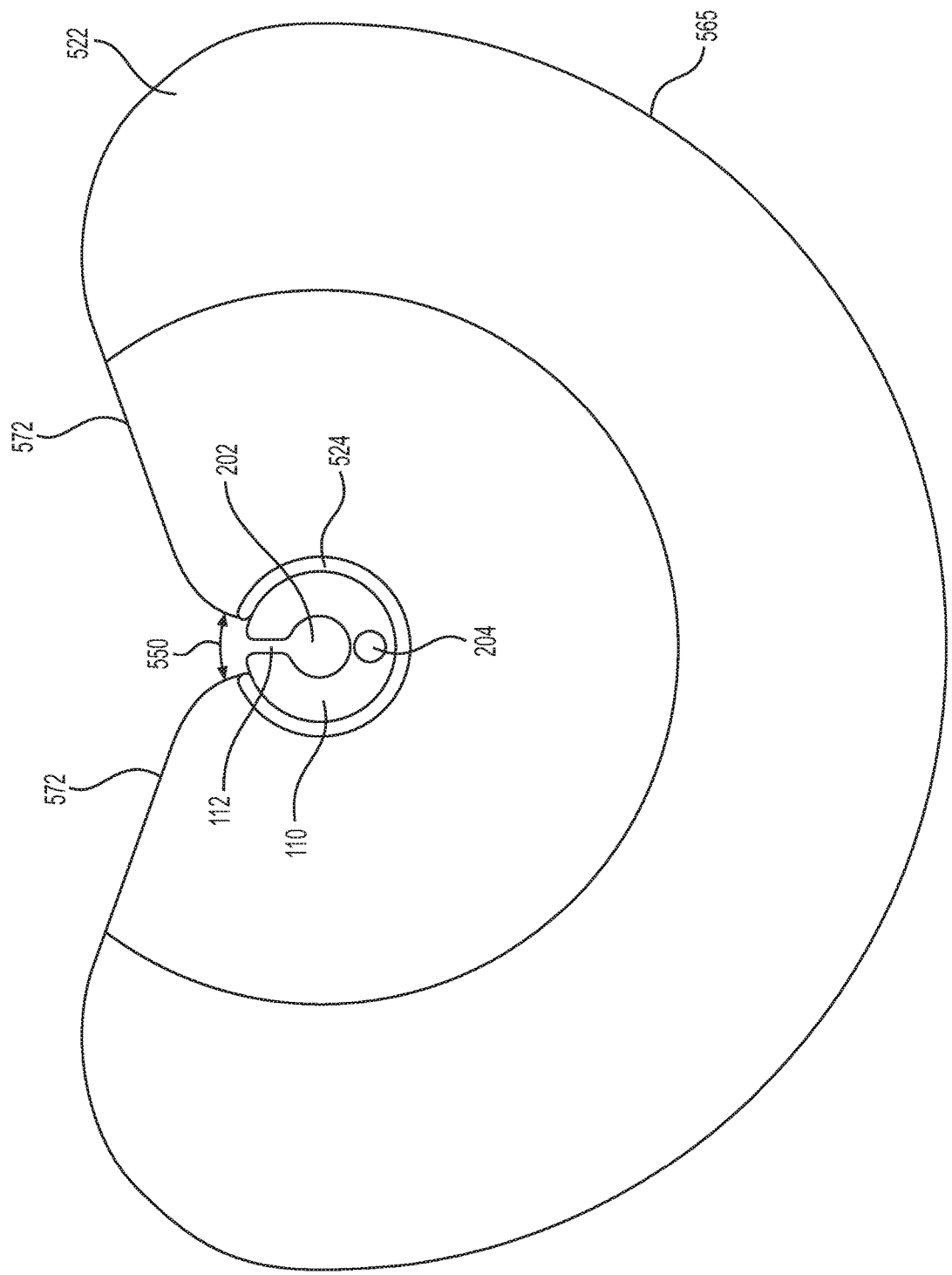
FIG. 5E is an end view of the exemplary balloon catheter of FIG. 5D as viewed in the proximal direction, according to embodiments of the present disclosure.

FIG. 5D is a perspective view of the distal portion of balloon catheter 500, with balloon 520 in an inflated state. FIG. 5E is an end view thereof as viewed in the proximal direction. When balloon 520 assumes the inflated state, inflatable portion 522 may be inflated while seal ends 524 and 526 remain deflated, due to the bonding between layers therein. Inflatable portion 522 may include two inward extensions 572, which may extend between catheter body 110 and an outer-most surface 565 of balloon 520. The discontinuity between extensions 572 may be substantially V-shaped, such that the distance between them is smaller the closer they are positioned to catheter body 110. Balloon 520 may be asymmetrical when in the inflated state due to, at least in part, the presence of the discontinuity between extensions 572. In some embodiments, balloon 520 may be constructed of a compliant material. Therefore, outer surface 565 may conform to a shape of a body lumen in which catheter 500 may be inserted.

Figure 6A:
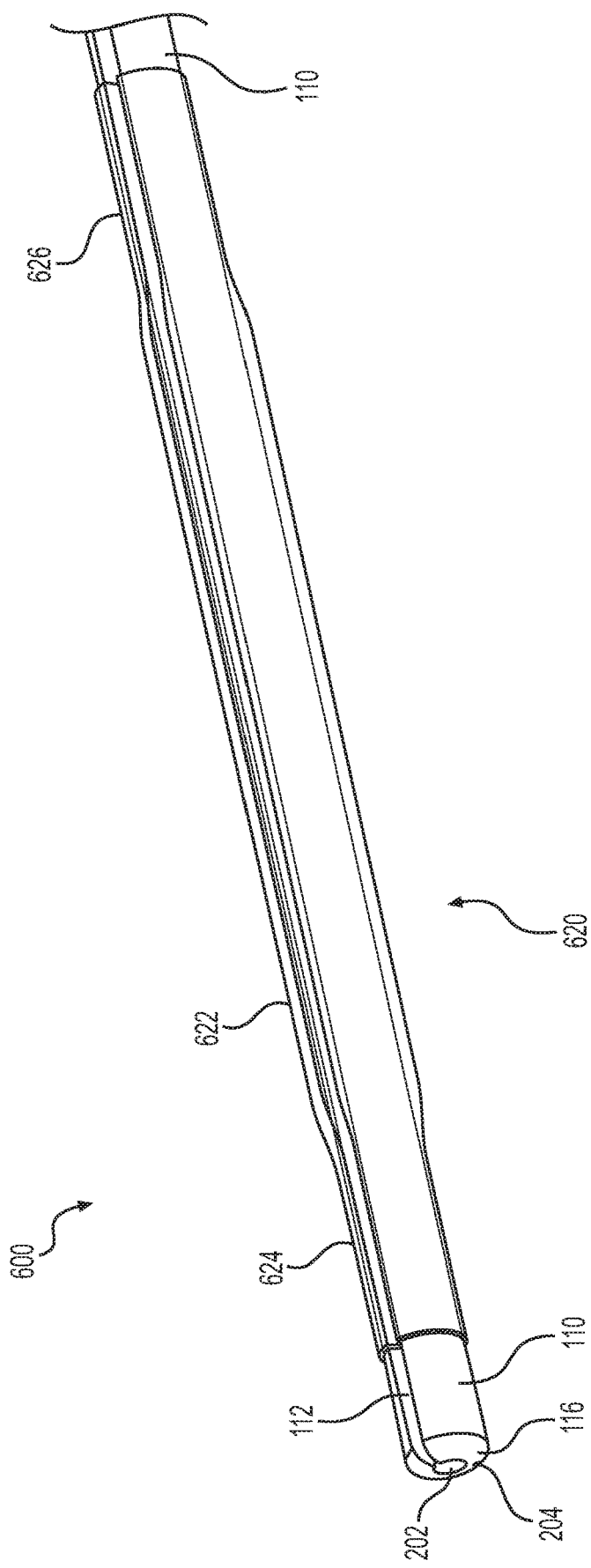
FIG. 6A is a perspective view of a distal portion of yet another exemplary balloon catheter, according to embodiments of the present disclosure.
Figure 6B:
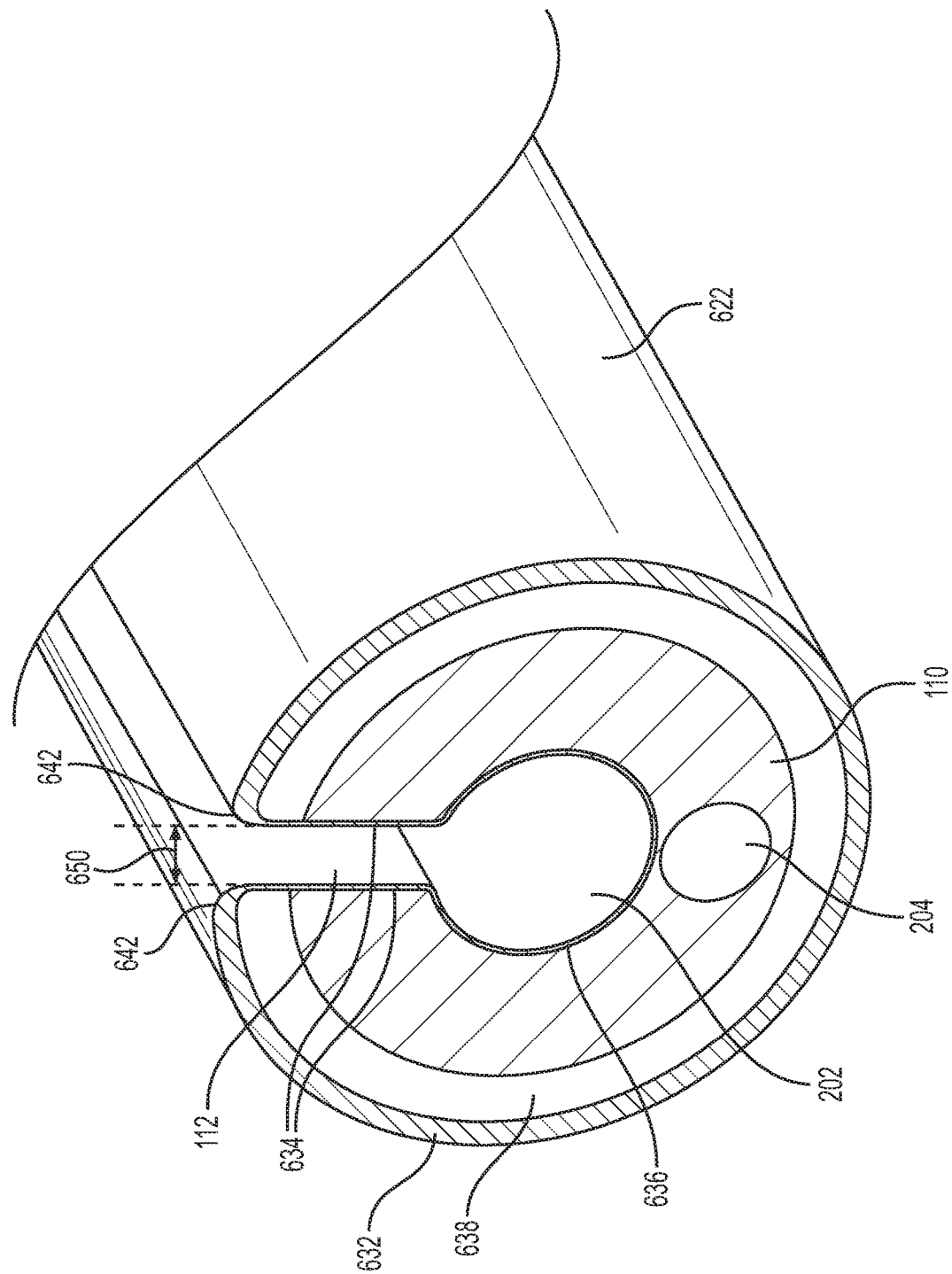
FIG. 6B is a perspective view of a cross-section of the exemplary balloon catheter of FIG. 6A, according to embodiments of the present disclosure.

FIG. 6A is a perspective view of a distal portion of an exemplary balloon catheter 600, according to various embodiments of the present disclosure. FIG. 6B is a perspective view of a cross-section of balloon catheter 600, in which balloon 620 is in a deflated state. Balloon catheter 600 may include catheter body 110 and balloon 620 affixed to a distal portion thereof. Balloon 620 may be formed by a single layer of compliant material. The single layer may be circumferentially wrapped about catheter body 110, and a portion thereof inserted through slit 112 into guidewire lumen 202. The single layer may include outer portion 632, which may extend circumferentially about a portion of catheter body 110. Additionally, the single layer may include guidewire portion 636, which may abut the wall of guidewire lumen 202, and slit portions 634, which may abut the walls of slit 112. Slit portions 634 may be bonded to slit 112 according to aforementioned techniques. Alternatively or additionally, guidewire lumen portion 636 may be bonded to the wall of guidewire lumen 202 according to aforementioned techniques. As a result, balloon 620 may be secured to catheter body 110. According to some embodiments, outer portion 632, slit portions 634, and guidewire lumen portion 636 may be equal in thickness. According to some alternative embodiments, one or more of slit portions 634 and guidewire lumen portion 636 may have a smaller thickness than outer portion 632.

Balloon 620 may include inflatable portion 622, distal seal end 624, and proximal seal end 626. Seal ends 624, 626 may include portions of balloon 620 which are bonded to the outer surface of catheter body 110 using aforementioned techniques such that air is prevented from passing between them. This bonding of seal ends 624, 626 creates an air-tight seal for balloon 620. Inflatable portion 622 may be positioned between seal ends 624, 626 and may be a portion of balloon 620 which is not bonded to catheter body 110. Instead, inflatable portion 622 may include inflatable chamber 638, which is formed between outer portion 632 and the outer surface of catheter body 110. Inflatable chamber 110 may be sealed at its distal and proximal ends by seal ends 624, 626, and along its inner ends by the seal between slit portions 634 and slit 112 and/or by the seal between guidewire lumen portion 636 and the wall of guidewire lumen 202. According to some embodiments, inflatable chamber 638 does not extend into distal seal end 624 or proximal seal end 626 due to the fact that balloon 620 is bonded to catheter body 110 in these portions.

Balloon 620 may additionally include junctions 642, which may be the intersections between outer portion 632 and slit portions 634. Discontinuity 650 may extend circumferentially between the junctions 642, and may be the portion of catheter body 110 over which balloon 620 does not extend. According to some embodiments, discontinuity 650 may be equal in width or may have a slightly smaller width than the natural width of slit 112 due to the fact that slit portions 634 extend into slit 112. Slit 112 may be radially aligned with discontinuity 650. As a result, when a section of the guidewire is passed through slit 112, it may also be passed through discontinuity 650. According to some embodiments, when slit 112 is widened to allow passage of a portion of a guidewire therethrough, discontinuity 650 may also be widened, thus allowing passage of the guidewire through portion 208 of the slit and minimizing risk of damage to balloon 620 by the guidewire. The natural width of slit 112 may be significantly smaller than the diameter of a guidewire placed within guidewire lumen 202. Therefore, the guidewire may be securely retained within guidewire lumen 202 when slit 112 exhibits its natural width. According to some embodiments, the guidewire may be lubricated so as to not damage or otherwise impact balloon 620.

Figure 6C:
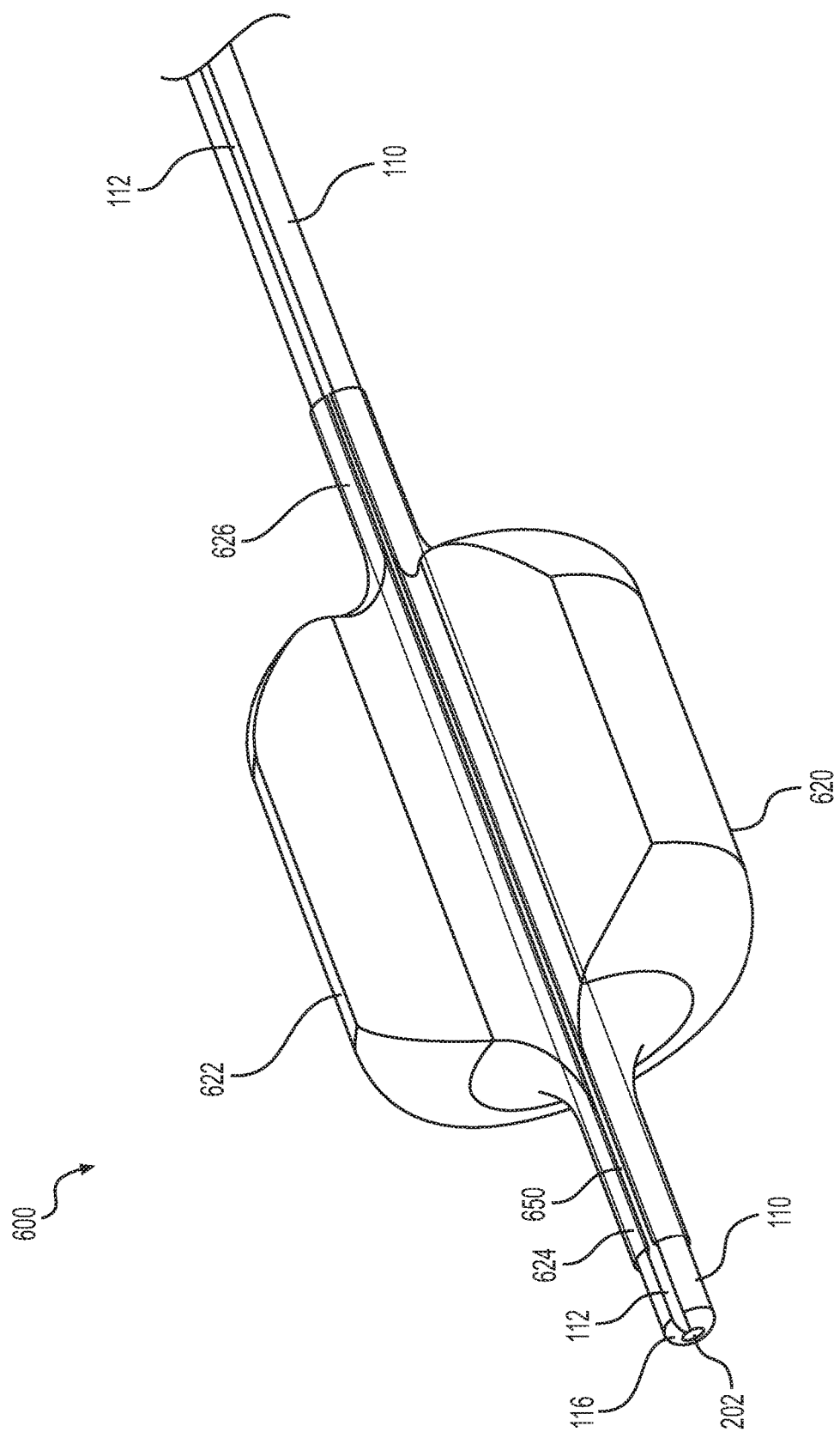
FIG. 6C is a perspective view of the distal portion of the exemplary balloon catheter of FIG. 6A with a balloon in an inflated state, according to embodiments of the present disclosure.

FIG. 6C is a perspective view of the distal portion of balloon catheter 600, with balloon 620 in an inflated state. FIG. 6D is a cross-sectional view thereof as viewed in the proximal direction. When balloon 620 assumes the inflated state, inflatable portion 622 may be inflated while seal ends 624, 626 remain deflated, due to the bonding between balloon 620 and catheter body 110 therein. Inflatable portion 622 may include two inward extensions 672, which may extend between catheter body 110 and an outer-most surface 665 of balloon 620. The discontinuity between extensions 672 may be substantially V-shaped, such that the distance between them is smaller the closer they are positioned to catheter body 110. Balloon 620 may be asymmetrical when in the inflated state due to, at least in part, the presence of the discontinuity between extensions 672. In some embodiments, balloon 620 may be constructed of a compliant material. Therefore, outer surface 665 may conform to a shape of a body lumen in which catheter 600 may be inserted.

Figure 6E:
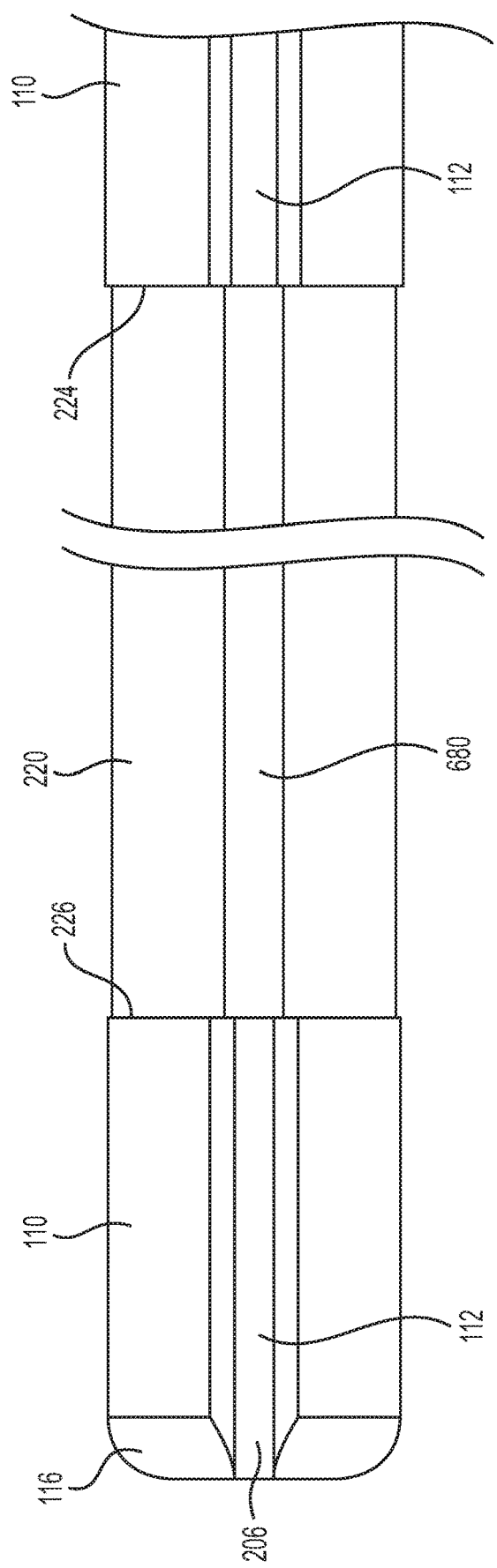
FIG. 6E is a top plan view of an exemplary catheter body of the exemplary balloon catheter of FIG. 6A, according to embodiments of the present disclosure.

FIG. 6E is a top plan view of the distal portion of catheter body 110 of balloon catheter 600, viewed without balloon 620 arranged thereon. Catheter body 110 may include depression 220. Balloon 620 may be positioned within depression 220. According to some embodiments, catheter body 110 may additionally include an expanded slit segment 680, in which the natural width of slit 112 is increased to accommodate slit portions 634. The natural width of slit 112 may be equal to the distance between slit portions 634 when they are inserted within expanded slit segment 680.

Figure 7D:
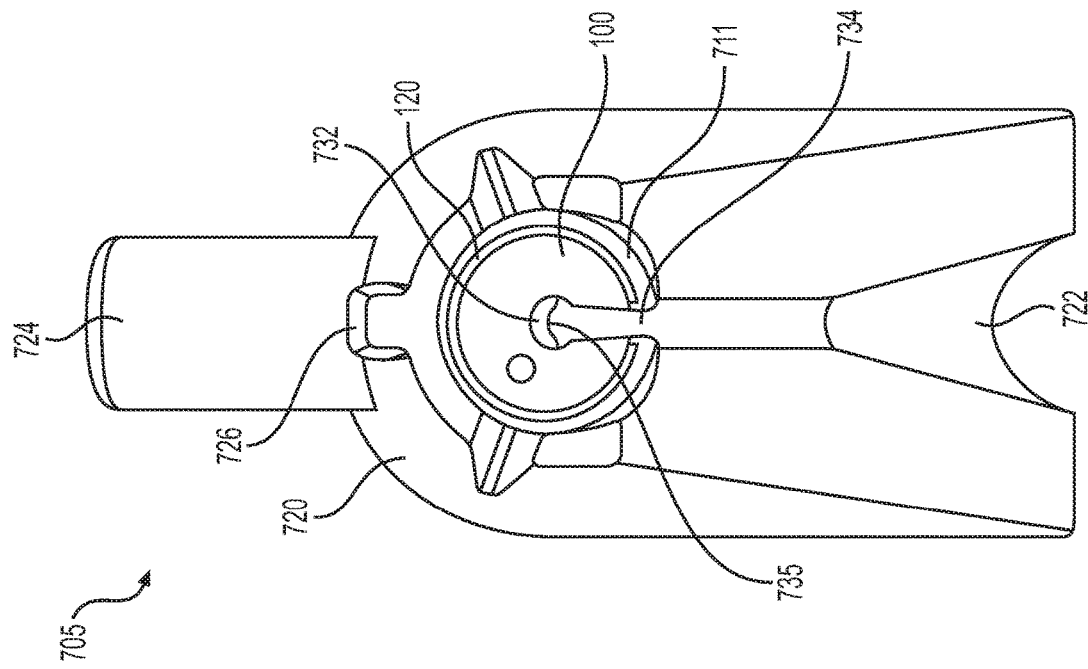
FIG. 7D is the bottom plan view of the exemplary adapter of FIG. 7A, with an exemplary balloon catheter inserted therein, according to embodiments of the present disclosure.
Figure 7C:
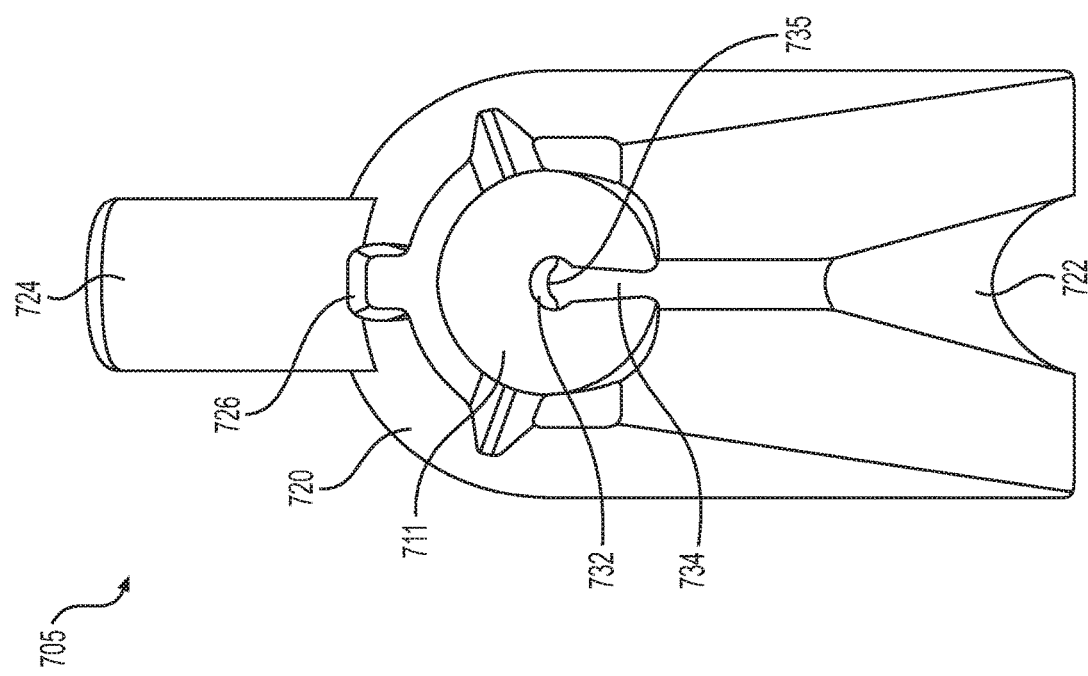
FIG. 7C is a bottom plan view of the exemplary adapter of FIG. 7A, according to embodiments of the present disclosure.

FIG. 7A is a perspective view of an exemplary adapter 705. FIG. 7B is a cross-sectional view of adapter 705. FIG. 7C is a bottom plan view of adapter 705. FIG. 7D is a bottom plan view of adapter 705 with an exemplary balloon catheter 100 inserted therein. Adapter 705 may receive balloon catheter 100 therein and may merge balloon catheter 100 onto a guidewire. Specifically, adapter 705 may receive balloon catheter 100 therein and may widen a portion of slit 112. A section of the guidewire may be passed through the widened portion of slit 112 and into guidewire lumen 202 of balloon catheter 100. One of ordinary skill in the art will understand that adapter 705 may be utilized for merging one or more of exemplary balloon catheters 400, 500, and 600 onto a guidewire.

Adapter 705 may include a tubular portion 710, a body 720, and a working member 730. Tubular portion 710 may be formed as a removable part or an integral part of adapter 705. A working channel 718 may extend longitudinally along the length of adapter 705, including along tubular portion 710 and body 720. Working channel 718 may include an opening 712 at a top end thereof, at the top end of tubular portion 710. Working channel 718 and opening 712 may be configured to receive balloon catheter 100 therein. Slits 714 and 716 may be diametrically positioned within tubular portion 710 and may extend longitudinally along the length of tubular portion 710. Balloon catheter 100 may be visible through slits 714 and 716 when it is positioned within working channel 718.

Tubular portion 710 may include first holder 711 and second holder 713. Holders 711 and 713 may be two deflectable halves of a clamping structure which may be configured to frictionally hold a portion of catheter 100, and may be separated by slits 714 and 716. Holders 711 and 713 may adaptively deflect inward or outward to receive and frictionally clamp onto portions of catheter 100 having different outer diameters. The clamping structure of tubular portion 710 reduces or prevents wiggling of catheter 100 as it passes through working channel 718.

When catheter 100 passes through working channel 718, holders 711 and 713 may frictionally hold at least a portion of catheter 100, thus securing it in place. Holders 711 and 713 include at least a portion of working channel 718 between them. In some embodiments, the inner surfaces of holders 711 and 713 may be configured to match the outer diameter of at least a portion of catheter 100. For example, the inner surfaces of holders 711 and 713 may form a substantially circular or spherical lumen which is substantially the same as the outer diameter of catheter 100. This allows a portion of catheter 100 to be frictionally held steady (e.g., by preventing catheter 100 from wiggling) as catheter 100 passes through working channel 718 to merge with guidewire 230 (not shown).

Working member 730 may be positioned within working channel 718 at an end thereof opposite opening 712. Working member 730 may include a wedge 731, a guide 732, and ramp 733. Wedge 731 may be a thin plate, such as a fin-shaped plate, that stems from the inner wall of working channel 718. Wedge 731 may extend to the center of working channel 718, where it may connect with guide 732. Guide 732 may be a tapered cylindrical structure, with a narrow end thereof facing upwards towards opening 712. The body of guide 732 may align with the longitudinal axis of working channel 718. The diameter of guide 732, at any longitudinal portion thereof, may be larger than the width of wedge 731. Ramp 733 may be positioned upon the top of wedge 731 and may provide a ramped surface between guide 732 and the inner wall of working channel 718. Working member 730 may open or widen slit 112 of balloon catheter 100 as it passes by, as described further below in reference to FIGS. 9A-9C. Additionally, when skive 114 of a catheter reaches ramp 733, ramp 733 may push the angularly cut portions of catheter body 110 away from working member 730, allowing the catheter to be dislodged from working member 730. As a result, the non-slitted portion of catheter body 110 may be passed through adapter 705 without interference from working member 730.

Body 720 may include side groove 722, which may extend along an angled face of body 720 and which may be configured to receive a guidewire therein. As illustrated in FIGS. 7C and 7D, a bottom end of side groove 722 may align with wedge 731 and guide 732. Side groove 722 may narrow as it extends towards the bottom of adapter 705. Adapter 705 may additionally include narrowed groove 734, which may extend along the bottom edge of working member 730 and which may serve as an extension of side groove 722. An angled portion 735 may be situated at the end of narrowed groove 734 and may include a curved body to angle the guidewire inserted therein in a downwards, longitudinal direction. Body 720 may additionally include protrusion 724, which may extend outward from an outer surface of body 720. Protrusion 724 may be generally cylindrical. Adapter 705 may additionally include bar 726, which may be a protrusion extending outward from the outer surface of body 720, and/or one or more grooves 728, which may be formed between the outer surface of body 720 and working channel 718.

As depicted in FIG. 7D, balloon catheter 100 may be inserted within working channel 718 and may engage working member 730. In some embodiments, wedge 731 may extend through slit 112, with guide 732 positioned within guidewire lumen 202. A guidewire may pass along side groove 722 and narrowed groove 734, and may be angled downward by angled portion 735. As a result, as balloon catheter 100 is passed through working channel 718, guidewire lumen 202 may be merged onto the guidewire.

FIG. 8A is a component view of an exemplary system 800 for merging a balloon catheter 100 onto a guidewire 230. One of ordinary skill in the art will understand that system 800 may be utilized for merging one or more of exemplary balloon catheters 400, 500, and 600 onto a guidewire 230. FIG. 8B is a perspective view of system 800. System 800 may be used in combination with an exemplary endoscope during an endoscopic procedure. System 800 includes adapter 705, an endoscopic block 820, and at least one balloon catheter 100. Adapter 705 may be fixedly or removably engaged with endoscopic block 820 and may be configured to receive balloon catheter 100 therein to be introduced over guidewire 230. Endoscopic block 820 may include a main body portion 830 and a fastener (not shown) which may affix endoscopic block 820 to an exemplary port of the endoscope. The port may be, for example, a biopsy port of the endoscope, which may provide access to a working channel of the endoscope. The port may be normally closed by a biopsy valve before use.

Adapter 705 and endoscopic block 820 may include one or more complementary fitting structures which may allow adapter 705 to fixedly or removably engage with endoscopic block 820. For example, adaptor 705 may removably engage with endoscopic block 820 via frictional fit, threaded fit, snap fit, etc. In some embodiments, body 720 of adapter 705 may be fitted within an opening of a main channel 832 of endoscopic block 820. For example, body 720 may be jammed in the opening of main channel 832, thereby securing adapter 705 on endoscopic block 820. In some embodiments, the user may clamp holders 711 and 713 against catheter 100 during insertion of body 720 into main channel 832, thus securing catheter 100 in place relative to adapter 705. Adapter 705 and endoscopic block 820 may further include other complementary fitting structures. In some embodiments, protrusion 724 of adapter 705 may engage with a clamp 834 of endoscopic block 820. Alternatively or additionally, bar 726 and grooves 728 may engage with complementary channels or protrusions (not shown) in the interior surface of main channel 832. Other suitable mechanical structures may be used alone or in combination with the above-described fitting structures to engage adapter 705 with endoscopic block 820. For example, a detent structure or a fastener may be used to engage adapter 705 with endoscopic block 820. Accordingly, adaptor 705 may be securely held in endoscopic block 820 during the introduction of balloon catheter 100 over guidewire 230.

Endoscopic block 820 may additionally include a groove 836, which may provide a path for guidewire 230, and a locking device 840 for fixing guidewire 230 in a desired position. Groove 836 may incline from locking device 840 towards the longitudinal axis of main channel 832 such that guidewire 230 is led to be aligned with the longitudinal axis of main channel 832 at a distal end of groove 836. This alignment may permit balloon catheter 100 to be introduced over guidewire 230 as it passes through working channel 718 of adapter 705, as further described below in reference to FIGS. 9A-9C.

More than one guidewires may be received and held in main channel 832. In some embodiments, main channel 832 may include at least one secondary groove for fixing at least one secondary guidewire in a desired position. Guidewire 230 and the secondary guidewire may be held to maintain access to the same treatment site or to different treatment sites, for example. In such instances, endoscopic block 820 may include at least one additional locking device 840 for locking the secondary guidewire in place. In some embodiments, different elongated devices, including balloon catheter 100, may be introduced over guidewire 230 and the secondary guidewire to perform different operations to the same treatment site or to perform different operations to different treatment sites. In other embodiments, the same elongated device, such as balloon catheter 100, may be introduced over guidewire 230 and over the secondary guidewire to perform the same operations to different treatment sites.

Locking device 840 may include zigzag locking features which may fix guidewire 230 in a desired position by frictionally maintaining guidewire 230 in place. For example, the zigzag locking features of locking device 840 may include a plurality of gaps 842 and slots 844. The size of gaps 842 and slots 844 may be approximately the same or smaller than the diameter of guidewire 230 such that guidewire 230 may be frictionally held in place by passing through gaps 842 and slots 844. In some embodiments, the zigzag locking features of locking device 840 may be used in combination with other mechanical features that can bend, twist, pinch, clamp, or lock guidewire 230 in place.

In some embodiments, balloon catheter 100 may be passed through working channel 718 of adapter 705 along the longitudinal axis thereof. Guidewire 230 may be merged into slit 112 of balloon catheter 100 when balloon catheter 100 passes by working member 730, which may open or widen slit 112 to receive the nearby portion of guidewire 230 there through. When balloon catheter 100 is inserted though working channel 718, the distal tip 116 of balloon catheter 100 may pass by working member 730. Wedge 731 of working member 730 opens up or widens slit distal end 206, thereby allowing guidewire 230 to merge into slit 112. Wedge 731 also maintains the opening of slit 112 as balloon catheter 100 passes by working member 730, thereby allowing for continuous merging of guidewire 230 into slit 112. Guide 732 may enter balloon catheter 100, such as guidewire lumen 202, to maintain the direction of insertion of balloon catheter 100 during its merge with guidewire 230. After the portion of slit 112 passes through working member 730, it returns to its natural width out of its own elasticity. Guidewire 230 may further merge into guidewire lumen 202 of balloon catheter 100. Balloon catheter 100 may be removed off guidewire 230 by being continuously split or torn away from guidewire 230 through slit 112 while guidewire 230 remains fixed by locking device 840.

In some embodiments, when adapter 705 is engaged with endoscopic block 820, side groove 722 of adapter 705 may complement main groove 836 of endoscopic block 820 to provide a path for leading guidewire 230 towards main channel 832. In some embodiments, side groove 722 may extend up to angled portion 735 of adapter 705 such that guidewire 230 may be directed downwards along the longitudinal axis of adapter 705. This may permit guidewire 230 to be aligned with balloon catheter 100 when balloon catheter 100 passes through working channel 718 along the longitudinal axis of adapter 705, thereby naturally merging into balloon catheter 100 as balloon catheter 100 passes by working member 730 at angled portion 735.

FIGS. 9A-9C are perpendicular cross-sectional views of system 800 at different stages of merging balloon catheter 100 onto guidewire 230. According some embodiments, before introducing balloon catheter 100 over guidewire 230, guidewire 230 may introduced to a treatment site by a first device such as a cannula or a sphincterotome and may be locked by locking device 840 in a predetermined position to maintain access to the treatment site. As shown in FIGS. 9A-9C, after passing through the locking features of locking device 840, guidewire 230 may be received in a path formed by main groove 836 and side groove 722 and led towards angled portion 735 of adapter 705.

As shown in FIG. 9A, to introduce balloon catheter 100 over guidewire 230, a physician or an assistant may insert balloon catheter 100 into working channel 718 of adapter 705. According to some embodiments, balloon catheter 100 may be inserted into adapter 705 prior to insertion of adapter 705 into endoscopic block 820. According to alternative embodiments, adapter 705 may be inserted into endoscopic block 820 prior to insertion of balloon catheter 100 into adapter 705. In some embodiments, to facilitate the alignment of balloon catheter 100 with working member 730 and/or guidewire 230, the inner diameter of working channel 718 may be selected to substantially match and/or to be slightly larger than an outer diameter of balloon catheter 100. As balloon catheter 100 passes through working channel 718, distal tip 116 meets and passes by working member 730, which then wedges open a portion of slit 112, such as slit distal end 206. As shown in FIG. 9B, this in turn allows a portion of guidewire 230 at angled portion 735 to merge into a corresponding portion of balloon catheter 100, e.g., a portion of guidewire lumen 202, through the opened portion of slit 112. After guidewire 230 merges into the distal end of balloon catheter 100, as shown in FIG. 9C, guidewire 230 can continuously merge into balloon catheter 100 as balloon catheter 100 passes though working channel 718 until the entire length of guidewire lumen 202 has been merged onto guidewire 230 or until the distal end of balloon catheter 100 approximates or reaches the desired treatment site. In various embodiments, when the entire length of guidewire lumen 202 has been merged onto guidewire 230, skive 114 may reach or approximate working member 730. Ramp 733 may dislodge balloon catheter 100 from working member 730. Therefore, a user or practitioner may continue introducing balloon catheter 100 through adapter 705 and into endoscopic block 820 without catheter movement being impeding by working member 730. Balloon catheter 100 may be introduced over guidewire 230 through main channel 832 and into the working channel of the endoscope, through which balloon catheter 100 may introduced until it reaches or approximates the desired treatment site.

As described above, guidewire 230 is held in place by locking device 840 throughout the merging of guidewire 230 into balloon catheter 100. This advantageously reduces the risk of losing the access to the desired treatment site in the body of a patient and increases the effectiveness of the introduction of balloon catheter 100 over guidewire 230 in a minimum amount of time.

According to various embodiments, to retrieve balloon catheter 100 introduced over guidewire 230, a physician or an assistant may remove adapter 705 from endoscopic block 820 and pull balloon catheter 100 out of the lumen of the endoscope and main channel 832. Guidewire 230 can remain locked by locking device 840 so that another elongated device may be introduced to the treatment site. During the retrieval of balloon catheter 100, to remove balloon catheter 100 off guidewire 230, the physician or assistant may separate balloon catheter 100 from guidewire 230 by continuously splitting or tearing balloon catheter 100 from guidewire 230 through slit 112.

Exemplary apparatuses, systems, and methods of the present disclosure may provide a number of benefits over prior apparatuses, systems, and methods, including prior endoscopic balloon catheters. As explained above, prior balloon catheters may only be introduced onto guidewires by unlocking the guidewire from its locking device and inserting the distal end of the balloon catheter onto the proximal tip of the guidewire. This unlocking of the guidewire can result in movement or displacement of the distal end of the guidewire and thus loss of access to the treatment site. This insertion process is also time- and energy-consuming for the physician or practitioner. In contrast, according to various embodiments of the present disclosure, an exemplary balloon catheter may be merged onto a guidewire via the slit in the balloon catheter, while the guidewire remains locked in the locking device of the endoscopic block. The balloon catheter may then be delivered to the desired treatment site via the guidewire, where it may be inflated to perform one or more procedures, such as removal of a body or stone or dilation of a tubular body structure. The balloon catheter may then be removed from the desired treatment site and split off of the guidewire. Advantageously, exemplary apparatuses, systems, and methods may allow the guidewire to remain locked during balloon catheter insertion, use, and removal, thus ensuring that access to the desired treatment site is maintained. Additionally, merging of the balloon catheter onto the guidewire may be easier to perform and may require less time than the merging of prior devices.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented as hardware alone. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A balloon catheter for medical procedure, the catheter comprising:
    a flexible, elongated catheter body including an inflation lumen and a guidewire lumen configured to receive a guidewire therein;
    an inflatable balloon affixed to the catheter body at a location proximal of a distal end of the guidewire lumen; and
    a slit passing between the guidewire lumen and an exterior surface of the catheter body, the slit extending continuously from the distal end of the guidewire lumen to a position along the catheter body proximal of the balloon, wherein
    the exterior surface of the catheter body includes at least one depression, the balloon being at least partially situated within the at least one depression, and
    the guidewire lumen is configured to retain the guidewire therein when the balloon is in a fully-inflated state.

2. The catheter of claim 1, wherein a natural width of the slit is substantially smaller than the diameter of the guidewire.

3. The catheter of claim 1, wherein the slit is configured to be temporarily widened to permit passage of a portion of the guidewire therethrough.

4. The catheter of claim 1, wherein an outer surface of the balloon is configured to be substantially even with the exterior surface of the catheter body when the balloon is deflated.

5. The catheter of claim 1, further comprising:
    a discontinuity in an outer surface of the balloon, the discontinuity extending longitudinally along the length of the outer surface of the balloon.

6. The catheter of claim 5, wherein the slit is radially aligned with the discontinuity.

7. The catheter of claim 1, wherein the balloon includes an aperture in a surface thereof, the aperture being aligned with an inflation hole in the catheter body.

8. The catheter of claim 1, wherein the balloon comprises:
    a single layer of compliant material with two edges arranged parallel to the slit, the two edges bonded to the exterior surface of the catheter body.

9. The catheter of claim 8, wherein the two edges are equidistant from the slit.

10. The catheter of claim 8, wherein a proximal edge and a distal edge of the single layer of compliant material are bonded to the exterior surface of the catheter body.

11. The catheter of claim 1, wherein the balloon comprises:
    an inner layer which is bonded to the exterior surface of the catheter body; and
    an outer layer bonded to the inner layer at proximal and distal ends of the outer layer, wherein
    the outer layer and the inner layer form an inflatable chamber.

12. The catheter of claim 11, wherein an entire inner surface of the inner layer is bonded to the catheter body.

13. The catheter of claim 11, wherein the inner layer and the outer layer are formed by a single sheet of compliant material.

14. The catheter of claim 11, wherein the inner layer is thinner than the outer layer.

15. The catheter of claim 1, wherein the balloon comprises a single layer of compliant material including:
    a first portion which extends about at least a portion of the exterior surface of the catheter body; and
    a second portion which passes through the slit and into the guidewire lumen.

16. The catheter of claim 15, wherein the second portion is bonded to a wall of the guidewire lumen and to the slit.

17. The catheter of claim 15, wherein the first portion is thicker than the second portion.

18. The catheter of claim 15, wherein a portion of the slit through which the single layer of compliant material passes has a larger natural width than one or more portions of the slit through which the single layer of compliant material does not pass.

19. An apparatus for removable engagement with a guidewire, the apparatus comprising:
    a catheter comprising:
        a flexible, elongated catheter body including an inflation lumen and a guidewire lumen;
        an inflatable balloon affixed to the catheter body; and
        a slit passing between the guidewire lumen and an exterior surface of the catheter body, the slit extending from a distal end of the guidewire lumen to a position along the catheter body proximal of the balloon; and
    an adapter configured to merge the catheter onto a guidewire, the adapter comprising:
        an adapter lumen configured to receive the catheter body and the balloon;
        a side groove extending along an outer surface of the adapter, the side groove configured to receive the guidewire and to align a portion of the guidewire with the adapter lumen; and
        a wedge extending from an inner surface of the adapter lumen, the wedge configured to widen a portion of the slit for passage of the aligned portion of the guidewire through the widened portion of the slit and into the guidewire lumen of the catheter.

20. The apparatus of claim 19, wherein the widened portion of the slit is configured to return to a natural width after passage of the guidewire therethrough such that the guidewire is retained within the catheter body.

21. The apparatus of claim 19, wherein the adaptor is configured for at least one of fixed engagement or removable engagement with an endoscopic block, the block configured to retain one or more guidewires.

22. The apparatus of claim 19, wherein the adaptor further comprises:
  at least one holder configured to hold at least a portion of the catheter.

23. A method for merging a balloon catheter onto a guidewire, the method comprising:
  obtaining a catheter, the catheter comprising:
    a flexible, elongated catheter body including an inflation lumen and a guidewire lumen;
    an inflatable balloon affixed to the catheter body; and
    a slit passing between the guidewire lumen and an exterior surface of the catheter body, the slit extending from a distal end of the guidewire lumen to a position along the catheter body proximal of the balloon;
  obtaining an adapter configured to merge the catheter onto a guidewire, the adapter comprising:
    an adapter lumen configured to receive the catheter body and the balloon;
    a side groove extending along an outer surface of the adapter, the side groove configured to receive the guidewire and to align a portion of the guidewire with the adapter lumen; and
    a wedge extending from an inner surface of the adapter lumen;
  receiving the catheter within the adapter lumen and engaging the catheter with the wedge to widen a portion of the slit; and
  merging the aligned portion of the guidewire into the guidewire lumen of the catheter through the widened portion of the slit.

24. The method of claim 23, further comprising:
  passing the catheter over the wedge and onto the guidewire until the guidewire extends through an entire length of the guidewire lumen; and
  passing the catheter body through the adapter lumen and over the guidewire until a distal end of the catheter reaches a desired treatment site.

25. The method of claim 23, further comprising:
  passing the catheter over the wedge and onto the guidewire until a distal end of the catheter reaches a desired treatment site.

26. The method of claim 25, further comprising:
  inflating the balloon at the desired treatment site.

27. The method of claim 23, further comprising:
  before merging the aligned portion of the guidewire into the guidewire lumen, engaging the adapter with an opening of an endoscopic block, wherein the guidewire is retained by the endoscopic block.

28. An adapter for merging a catheter onto a locked guidewire, comprising:
  means for receiving a catheter having an inflatable balloon affixed thereto, the catheter including a slit extending along at least a portion of the length of the catheter to a position proximal of the balloon;
  means for aligning a portion of a locked guidewire with the catheter, without unlocking the guidewire; and
  means for widening a portion of the slit of the catheter such that the aligned portion of the locked guidewire merges into the catheter through the widened portion of the slit.

29. The apparatus of claim 19, wherein the inflatable balloon is affixed to the catheter body at a location proximal of the distal end of the guidewire lumen.

30. The method of claim 23, wherein the inflatable balloon is affixed to the catheter body at a location proximal of the distal end of the guidewire lumen.

* * * * *